United States Patent
Hutcheson et al.

(10) Patent No.: US 11,235,033 B1
(45) Date of Patent: Feb. 1, 2022

(54) MATERIALS AND METHODS FOR THE TREATMENT OF VASCULAR CALCIFICATION

(71) Applicants: Joshua Hutcheson, Miami, FL (US); Alexander Agoulnik, Miami, FL (US); Hooi Hooi Ng, Miami, FL (US)

(72) Inventors: Joshua Hutcheson, Miami, FL (US); Alexander Agoulnik, Miami, FL (US); Hooi Hooi Ng, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/092,024

(22) Filed: Nov. 6, 2020

(51) Int. Cl.
*A61K 38/00* (2006.01)
*A61K 38/22* (2006.01)
*A61P 9/10* (2006.01)
*A61K 31/517* (2006.01)
*A61K 31/167* (2006.01)

(52) U.S. Cl.
CPC ........ *A61K 38/2221* (2013.01); *A61K 31/167* (2013.01); *A61K 31/517* (2013.01); *A61P 9/10* (2018.01)

(58) Field of Classification Search
CPC .............. A61K 38/2221; A61K 31/167; A61K 31/517; A61P 9/10
See application file for complete search history.

(56) References Cited

U.S. PATENT DOCUMENTS

2017/0144984 A1* 5/2017 Marugan ............... C07C 257/04

OTHER PUBLICATIONS

Mohammed Akhter Hossain, A single-chain derivative of the relaxin hormone is a functionally selective agonist of the G proteincoupled receptor, RXFP1, Chem. Sci., 2016, 7, 3805-3819.*

* cited by examiner

*Primary Examiner* — James H Alstrum-Acevedo
*Assistant Examiner* — Erinne R Dabkowski
(74) *Attorney, Agent, or Firm* — Saliwanchik, Lloyd & Eisenschenk

(57) ABSTRACT

The subject invention provides molecules, compositions and methods for treating, preventing or ameliorating vascular calcification, for example, medial vascular calcification or intimal atherosclerotic calcification. The subject invention also provides molecules, compositions and methods for treating or preventing a disease associated with vascular calcification. The methods of the subject invention employ relaxin-based and/or epidermal growth factor receptor (EGFR)-based strategies through the use of RXFP1 agonists and/or EGFR inhibitors.

15 Claims, 10 Drawing Sheets
(10 of 10 Drawing Sheet(s) Filed in Color)

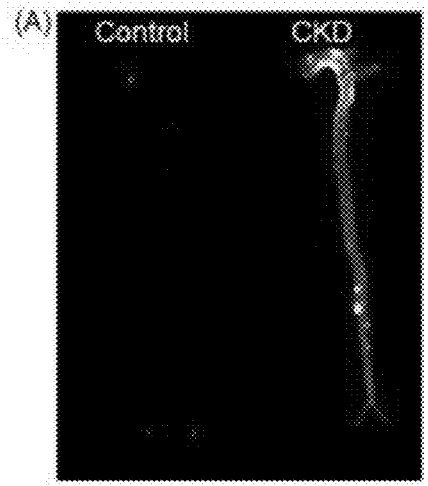
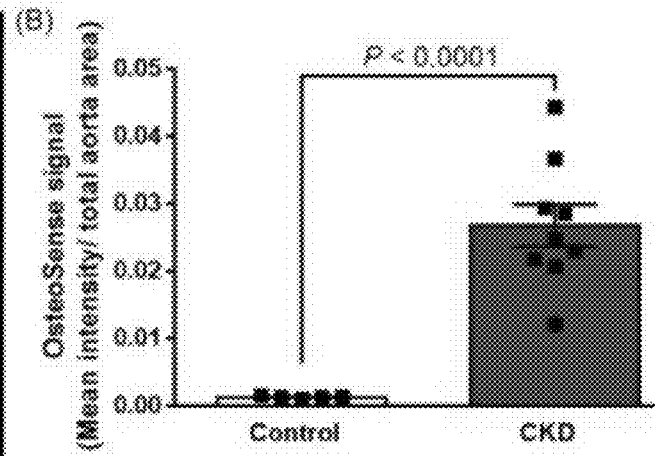
FIG. 1A    FIG. 1B
FIG. 2A    FIG. 2B
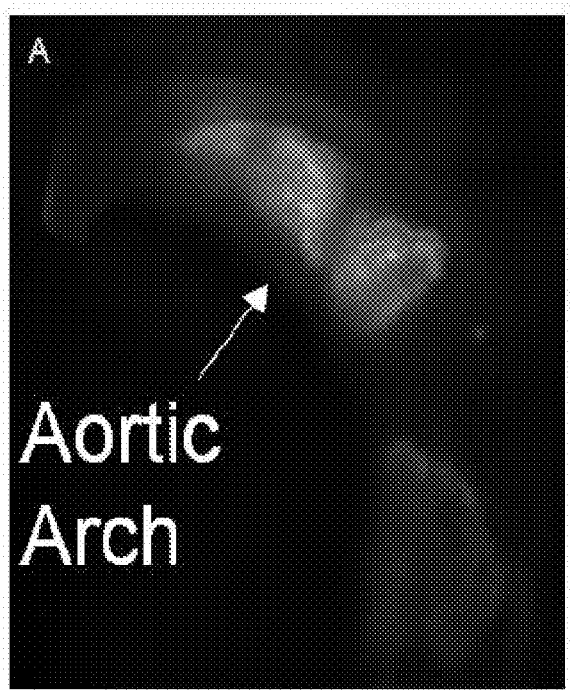
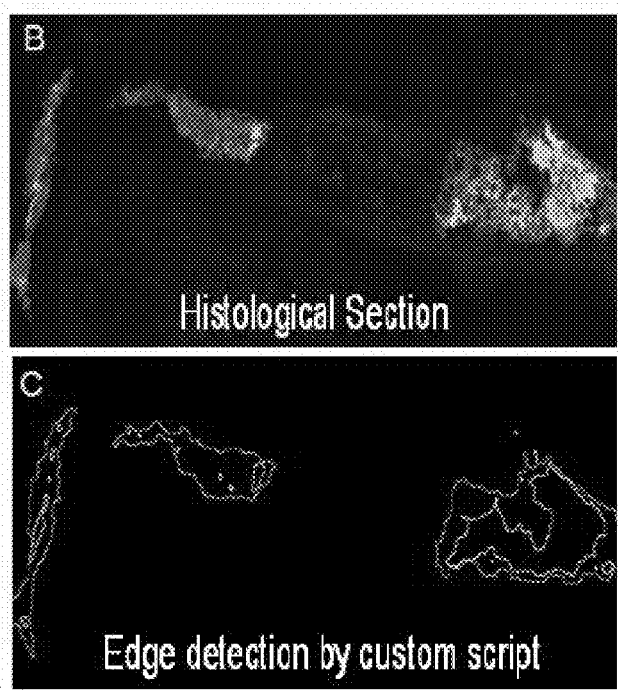
FIG. 2C FIG. 3A
FIG. 3B
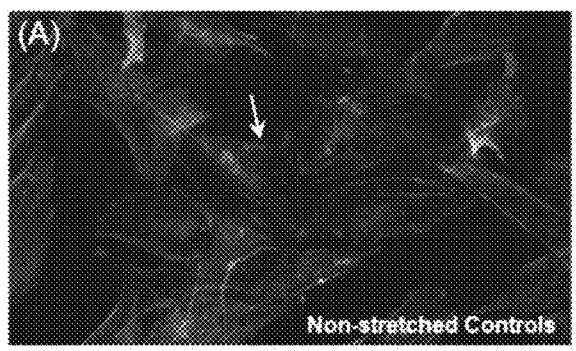
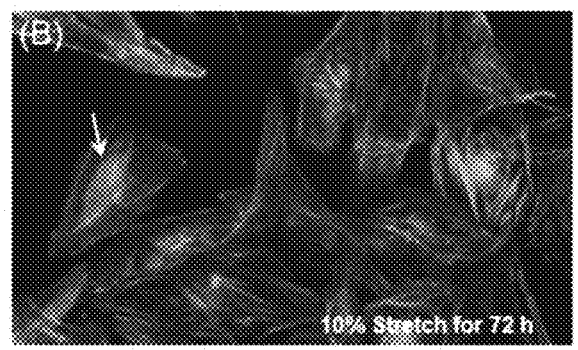
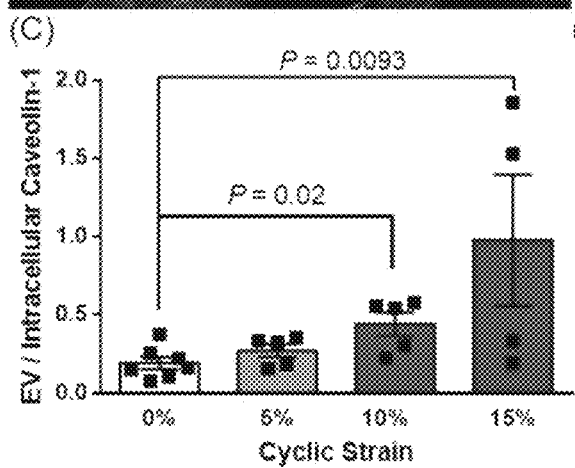
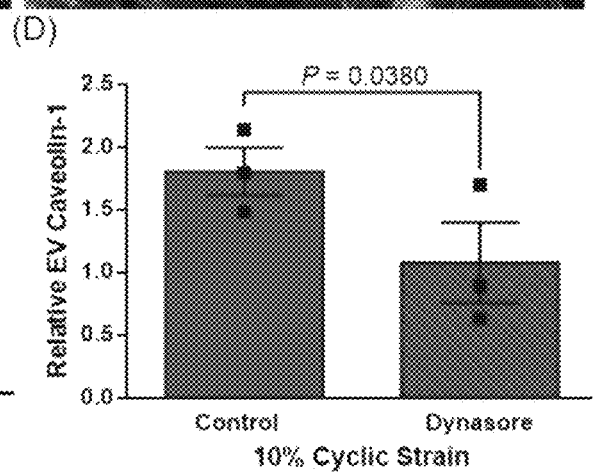
FIG. 3C
FIG. 3D FIG. 4A  FIG. 4B
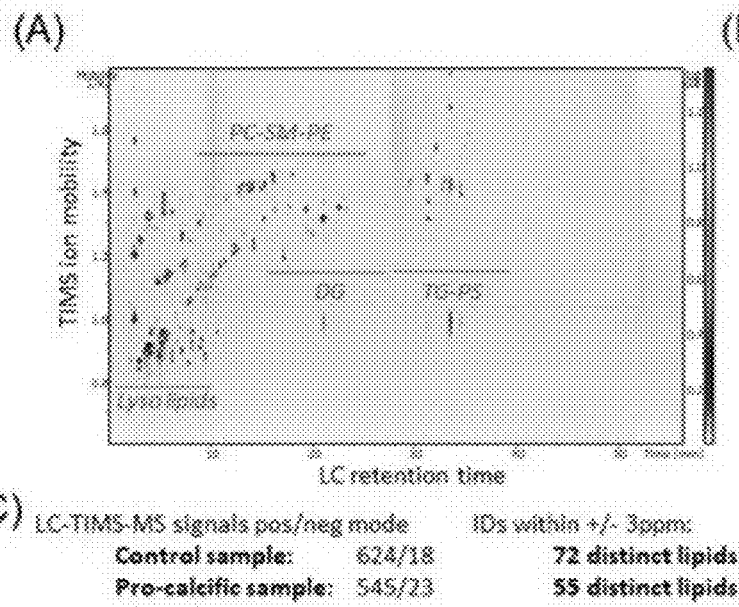
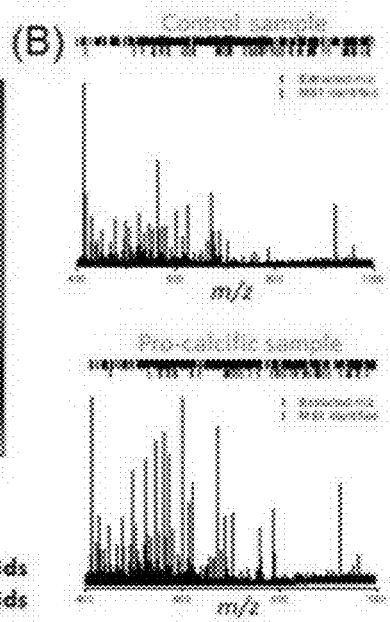
FIG. 4C
FIG. 5A  FIG. 5B  FIG. 5C FIG. 8A
FIG. 8B
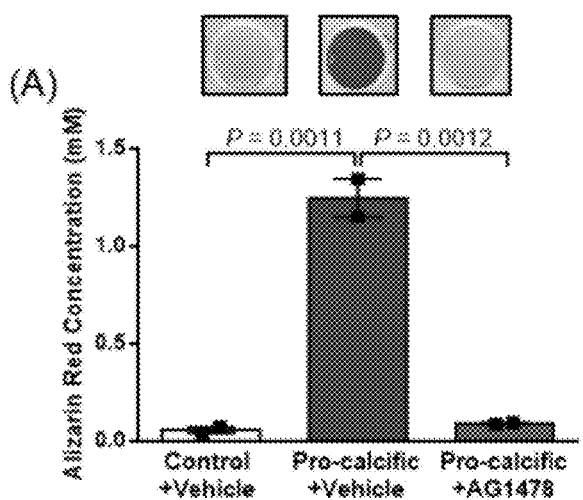
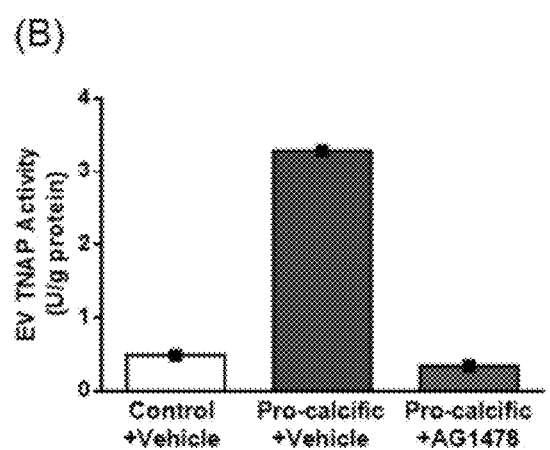
FIG. 8C
FIG. 8D
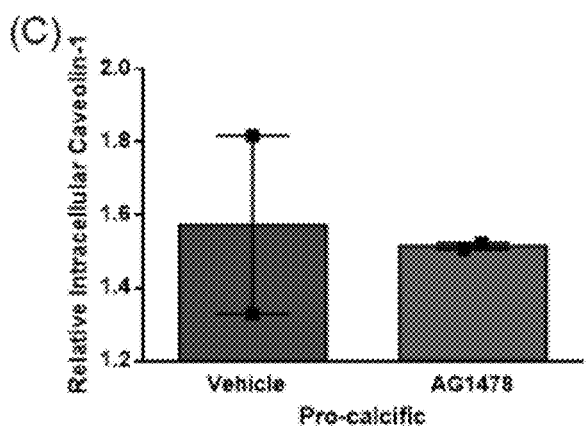
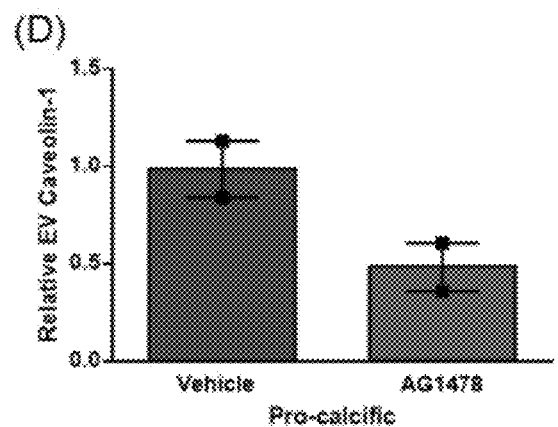
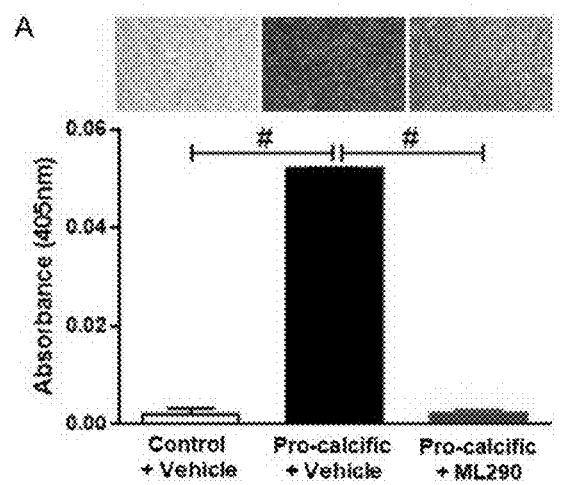
FIG. 9A

MATERIALS AND METHODS FOR THE TREATMENT OF VASCULAR CALCIFICATION

BACKGROUND OF THE INVENTION

Vascular calcification, the formation of bone-like mineral in blood vessel walls, is the leading indicator of cardiovascular morbidity and mortality. Calcification reduces vascular wall elasticity and promotes atherosclerotic plaque rupture, the leading cause of heart attacks and strokes. Coronary artery calcification is associated with a four-fold increase in cardiovascular events, and patients with aortic calcification are up to six times more likely to suffer cardiovascular mortality.

Types of vascular calcification include, for example, calcific atherosclerosis, calcific medial vasculopathy, elastocalcinosis, calcific uremic arterioloopathy, aalcific aortic valvular stenosis, and portal vein calcification. Vascular calcification is associated with a range of diseases, such as atherosclerosis, hyperlipidemia, osteoporosis, hypertension, inflammation, diabetes (e.g., type 2 diabetes mellitus (T2DM)), end-stage renal disease (ESRD), hyperphosphatemia, amputation, vitamin D disorders, vitamin K deficiency, Kawasaki disease, pseudoxanthoma elasticum (PXE), Marfan's Syndrome, Singleton-Merten syndrome, β-thalassemia, rheumatoid arthritis, congenital bicuspid valve, rheumatic heart disease, and liver disease.

The development of therapeutics for vascular calcification would significantly improve cardiovascular outcomes, especially in high risk populations such as those with chronic kidney disease (CKD). Patients with end-stage CKD exhibit rapid, widespread vascular calcification. Ongoing clinical studies seek to mitigate this calcification with a goal of improving cardiovascular outcomes. CKD patients with no detectable vascular calcification have 8 year all-cause survival rates of ~90% compared to 50% survivability in age-matched patients with medial calcification.

While vascular calcification can occur passively as a degenerative disorder during aging, it also involves active processes, in which smooth muscle cells (SMCs) undergo phenotypic modulation, acquire the expression of osteogenic proteins, and deposit a mineralized bone-like matrix. SMC-induced calcification involves the release of calcifying extracellular vesicles (EVs), a subpopulation traditionally known as matrix vesicles. Calcifying EVs bind calcium and generate free phosphate-two critical elements required to form pathological bone-like mineral in the arterial wall. Calcifying EV formation in SMCs occurs through mechanisms similar to exosomes, requiring neutral sphingomyelinase activity as the nascent vesicles traffic through the cell. However, the mechanisms through which EVs form within the cell and develop their mineral-promoting characteristics remain poorly understood.

Cell-cell communication throughout the body relies on exosomes to deliver content from one cell to another. Building on seminal mechanistic EV studies to develop treatments for vascular calcification will require targeting more specific aspects of the trafficking mechanisms that form calcifying EVs. Sphingomyelin metabolism also regulates caveolae internalization. Calcifying EV formation in SMCs requires the presence of caveolin-1,6 the main component of caveolae. These small membrane invaginations mediate intracellular trafficking and regulate plasma membrane mechanical tension. The function of caveolae in calcifying EV formation, however, is unclear.

There are currently no effective pharmacotherapies to prevent or treat vascular calcification. Conventional therapeutic approaches may involve in controlling serum phosphate while minimizing oral calcium load, for example, through a use of an adapted dialysate calcium concentration; use of phosphate-binding agents; the administration of calcitriol or vitamin D analogues; the use of calcimimetics; diet recommendations (reducing dietary phosphate intake and administering phosphate binders and calcium supplements); and/or the uptake of native vitamin D supplements.

Thus, there is a need for the development and identification of drugs for treating and preventing vascular calcification. There is a further need for developing methods for treating and preventing diseases associated with vascular calcification, e.g., medial vascular calcification or intimal atherosclerotic calcification.

BRIEF SUMMARY OF THE INVENTION

The subject invention provides compounds, compositions and methods for treating, preventing or ameliorating vascular calcification, for example, medial vascular calcification or intimal atherosclerotic calcification. The subject invention also provides compounds, compositions and methods for treating or preventing a disease associated with vascular calcification.

In one embodiment, the methods of the subject invention employ relaxin-based and/or epidermal growth factor receptor (EGFR)-based strategies for treating, preventing or ameliorating vascular calcification and diseases associated with vascular calcification. The compounds and compositions of the subject invention affect and control the mechanism by which extracellular vesicles (EVs) in smooth muscle cells (SMCs) obtain their mineralizing properties for vascular calcification.

In one embodiment, the methods of the subject invention are for treating, preventing or ameliorating cardiovascular calcification. In other embodiments, the method is for treating, preventing or ameliorating Mönckeberg's arteriosclerosis, calcific atherosclerosis, calcific medial vasculopathy, elastocalcinosis, aalcific aortic valvular stenosis, portal vein calcification and/or calcific uremic arteriolopathy (CUA).

In one embodiment, the subject invention provides a method for preventing and/or treating vascular calcification via the activation of a relaxin family peptide receptor (RXFP), e.g., RXFP1, and/or the inhibition of EGFR, the method comprising administering to a subject in need of such prevention and/or treatment a pharmaceutical composition comprising one or more compounds selected from RXFP agonists, e.g., small molecule RXFP1 agonists or peptides. In a further embodiment, the pharmaceutical composition may comprise one or more EGFR inhibitors. In preferred embodiments, the administration is local, oral, transdermal, or parenteral administration.

In one embodiment, the vascular calcification is cardiovascular calcification. In specific embodiments, the vascular calcification is medial vascular calcification or intimal atherosclerotic calcification.

In one embodiment, the subject is a human having been diagnosed with CKD, diabetes, hyperparathyroidism, hyperphosphatemia, a vitamin D disorder, a vitamin K disorder, osteoporosis, Kawasaki disease, arterial calcification due to deficiency of CD73 (ACDC), idiopathic basal ganglia calcification (IBGC), pseudoxanthoma elasticum (PXE), rheumatoid arthritis, Singleton-Merten syndrome, β-thalassemia, atherosclerosis, hyperlipidemia, hypertension, amputation, congenital bicuspid valve, and/or rheumatic heart disease.

In one embodiment, the subject invention provides a method for preventing and/or treating cardiovascular calcification via the activation of a RXFP1, the method comprising administering to a subject in need of such prevention and/or treatment a therapeutically effective amount of one or more RXFP1 agonists, or a pharmaceutical composition comprising one or more compounds selected from RXFP1 agonists.

In specific embodiments, the pharmaceutical composition comprises one or more molecules/compounds selected from small molecule RXFP1 agonists, relaxin peptides, relaxin varients, analogs, and derivatives thereof. In a further embodiment, the pharmaceutical composition may comprise one or more EGFR inhibitors.

In one embodiment, the subject invention provides a method for preventing or reducing mineral nucleation and deposition in vascular wall, e.g., cardiovascular wall, the method comprising administering to a subject in need of such prevention or reducing a pharmaceutical composition comprising one or more molecules selected from RXFP agonists, preferably, RXFP1 agonists, and EGFR inhibitors. In preferred embodiments, the administration is local, oral, transdermal, or parenteral administration. In a specific embodiment, the subject is a human having been diagnosed with CKD or atherosclerosis.

In one embodiment, the subject invention also provides a method for preventing or reducing the formation of calcifying EVs in SMCs, the method comprising contacting SMCs with a pharmaceutical composition comprising one or more molecules selected from RXFP agonists, preferably, RXFP1 agonists, and EGFR inhibitors. In a preferred embodiment, SMCs are obtained from a subject suffering from a disease associated with vascular calcification, e.g., CKD and atherosclerosis.

In one embodiment, the RXFP agonists are small molecules that can activate RXFP, preferably, RXFP1, more preferably, human RXFP1. In a preferred embodiment, the small molecule RXFP agonist is ML290 having a structure of

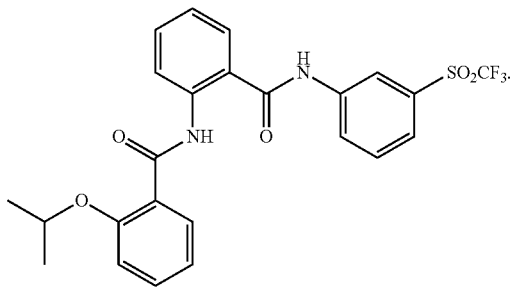

In one embodiment, the one or more EGFR inhibitors are selected from necitumumab; saracatinib; canertinib; dacomitinib; vandetanib; neratinib; erlotinib; gefitinib; afatinib; osimertinib; lapatinib; AG1478; AG490; CP724714; WZ4002; sapitinib; CUDC-101; PD153035; pelitinib; AEE788; AC480; OSI-420; WZ3146; Allitinib; Rociletinib; Varlitinib; Icotinib; TAK-285; WHI-P154; Daphnetin; PD168393; CNX-2006; Tyrphostin 9; AG-18; Epertinib; BI-4020; Tyrphostin AG-528; SU5214; RG 13022; TQB3804; TAS6417; Pyrotinib; PD153035; AG 494; AG 555; Theliatinib; Avitinib; Lazertinib; Lifirafenib; Nazartinib; Brigatinib; Tucatinib; AZD3759; CL-387785; Poziotinib; AZ5104; and Mobocertinib. In a preferred embodiment, the EGFR inhibitor is AG1478.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1B show that CKD mice exhibit widespread aortic calcification. Signal is quantified by Osteo Sense fluorescence intensity.

FIGS. 2A-2C show that serial injection of calcium tracing dyes allows for temporal tracking of mineral formation in an endpoint analysis in a single mouse.

FIGS. 3A-3D show that within SMCs, the caveolin-1 moves from A) membrane localization in non-stretched samples to B) the cytoplasm in stretched samples. C) Western blotting shows redistribution of caveolin-1 from intracellular (SMC) stores into EVs in response to mechanical stretch. D) Inhibition of dynamin reduces caveolin-1 release in EVs.

FIGS. 4A-4C show that A) LC-TIMS-MS identified various lipid species in calcifying EVs. B) Representative MS spectra of control and calcifying EVs. C) Distinct lipid profiles were observed in these samples.

FIGS. 5A-5C show that A) the schematic of EV translocation (1) and collision (2) events. B) Preliminary data showing signal changes induced by individual EVs from SMCs cultured under cyclic stretch. (C) A histogram of these EVs (n=429) shows a higher average potential, indicative of a more negative charge, compared to EVs from static culture (n=386).

FIGS. 8A-8D show that A) EGFR inhibition with 2.5 μM AG 1478 prevents SMC mineralization in vitro (n=3) and B) reduces EV TNAP activity (n=2). C) EGFR inhibition does not affect intracellular caveolin-1 (n=2), but D) reduces EV caveolin-1 (n=2).

FIGS. 9A-9D show that A) ML290 (5 μM) significantly reduces mineral formation by vascular smooth muscle cells in vitro. B) treating atherogenic Apoe−/− mice with ML290 through oral gavage (30 mg/kg, n=8 mice per group) reduces calcification in vivo. Lower OsteoSense fluorescence in mice treated with ML290 (oral gavage, 30 mg/kg) at either the beginning of the atherogenic diet (third aorta) or after 15 weeks of atherogenic diet (fourth aorta) indicates less mineral compared to vehicle treated controls (second aorta) after 25 weeks of atherogenic diet. A chow control is shown for comparison (first aorta). C) Quantification of mice treated with ML290 at the initiation of the atherogenic diet. Lower OsteoSense fluorescence in ML290 treated mice indicates less mineral compared to vehicle treated controls after 25 weeks of atherogenic diet. D) Quantification of OsteoSense signal in mice treated at 15 weeks of atherogenic diet, indicating potential of treatment to reverse existing remodeling. #p<0.0001.

DETAILED DESCRIPTION OF THE INVENTION

Figure 6:
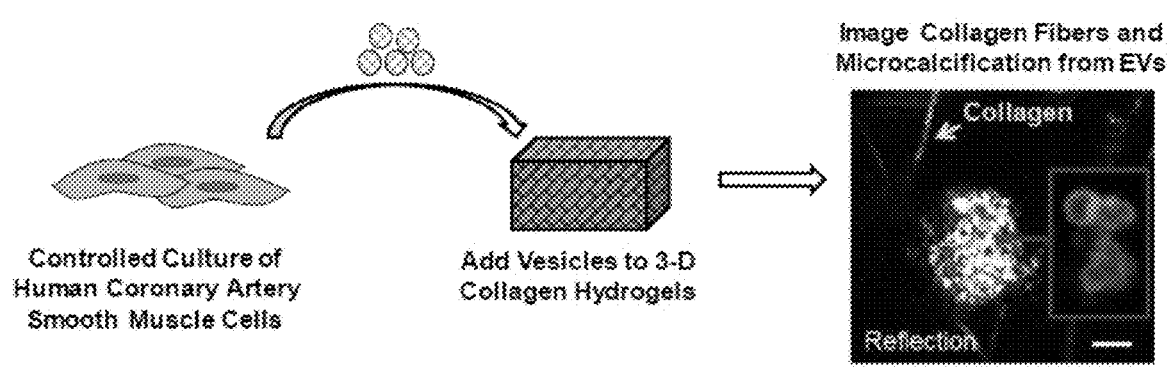
FIG. 6 shows that collagen hydrogel platform allows for imaging of calcification formation from EVs.

The subject invention provides compounds, compositions and methods for treating, preventing or ameliorating excess or inappropriate vascular calcification, for example, medial vascular calcification or intimal atherosclerotic calcification, in a subject. The subject invention also provides compounds, compositions and methods for treating or preventing a disease associated with vascular calcification in a subject.

In one embodiment, the methods of the subject invention employ relaxin-based and/or epidermal growth factor receptor (EGFR)-based strategies for treating, preventing or ameliorating vascular calcification and diseases associated with vascular calcification. The compounds and compositions of the subject invention affect and control the mechanism by which EVs in SMCs obtain their mineralizing properties for vascular calcification.

In one embodiment, the methods of the subject invention are for treating, preventing or ameliorating cardiovascular calcification. Specifically, in preferred embodiments, the compounds/molecules, and compositions target RXFP1 for preventing and treating cardiovascular calcification. In another embodiment, the method is for treating, preventing or ameliorating Mönckeberg's arteriosclerosis, calcific atherosclerosis, calcific medial vasculopathy, elastocalcinosis, aalcific aortic valvular stenosis, portal vein calcification and/or calcific uremic arteriolopathy (CUA).

In one embodiment, the subject is suffering from chronic kidney disease (CKD), diabetes, ageing, hyperparathyroidism, hyperphosphatemia, a vitamin D disorder, a vitamin K disorder, osteoporosis, Kawasaki disease, arterial calcification due to deficiency of CD73 (ACDC), generalized arterial calcification of infancy (GACI), idiopathic basal ganglia calcification (IBGC), pseudoxanthoma elasticum (PXE), rheumatoid arthritis, Singleton-Merten syndrome and/or β-thalassemia. Optionally, vascular calcification is associated with, for example, atherosclerosis, hyperlipidemia; hypertension; T2DM; ESRD; amputation; Marfan's Syndrome; congenital bicuspid valve; rheumatic heart disease; and liver disease.

Relaxin Family Peptide Receptor (RXFP) Agonists

The physiological effects of relaxin, a small peptide hormone, are mediated by its interaction with a G protein coupled receptor, RXFP, leading to the modulation of several signal transduction pathways. Activation of RXFP by relaxin induces: 1) up-regulation of the endothelin system that leads to vasodilation; 2) extracellular matrix remodeling through regulation of collagen deposition, cell invasiveness, proliferation, and overall tissue homeostasis; 3) a moderation of inflammation by reducing levels of inflammatory cytokines, such as TNF-αt and TGF-β: and 4) angiogenesis by activating transcription of VEGF.

Relaxin has therapeutic potential in treating fibrosis in kidney, liver, heart, vasculature and other organs. Chronic treatment with relaxin also improved arterial compliance in hypertensive rats. Although relaxin has been shown to be safe and well-tolerated in humans, a major problem with the application of peptide-based therapy to chronic diseases is the high cost and low stability of the peptide, e.g., the recombinant form of human relaxin, in vivo, thus requiring continuous intravenous (IV) delivery for extended time.

The term "relaxin" includes the naturally occurring peptide hormone relaxin, which is well known in the art, and non-endogenous human relaxin. Examples of endogenous relaxin include, but are not limited to, proteins associated with Relaxin 1 (RLN-1), Relaxin 2 (RLN-2), and Relaxin 3 (RLN-3) as well as with Relaxin/Insulin-Like Family Peptide Receptor (RXFP1) activity. The non-endogenous human relaxin, includes intact full length human relaxin or a portion of the relaxin molecule that retains biological activity. Also, contemplated for use according to the subject invention are human H1 preprorelaxin, prorelaxin, and relaxin; H2 preprorelaxin, prorelaxin, and relaxin; and H3 preprorelaxin, prorelaxin, and relaxin. The term "relaxin" further includes biologically active (also referred to herein as "pharmaceutically active") relaxin from recombinant, synthetic or native sources. Also, contemplated for use according to the subject invention are relaxin variants, such as amino acid sequence variants. As such, the subject invention encompasses the use of synthetic human relaxin and recombinant human relaxin, including synthetic H1, H2 and H3 human relaxin, recombinant H1, H2 and H3 human relaxin, peptide derivatives of relaxin, or other non-related to relaxin peptide activators of RXFP, preferably, RXFP1.

In one embodiment, RXFP agonists encompass active agents with relaxin-like activity, including, but are not limited to, relaxin, relaxin mimetics and/or relaxin analogs and portions thereof that retain biological activity, including all agents that competitively displace bound relaxin from a relaxin receptor. In some embodiments, the RXFP agonists activate one or more relaxin-related G-protein coupled receptors (GPCR), examples of which include, but are not limited to, RXFP1 (LGR7), RXFP2 (LGR8), RXFP3, RXFP4, FSHR (LGR1), LHCGR (LGR2), TSHR (LGR3), GPCR135, GPCR142, LGR4, LGR5, and LGR6. Molecules that can activate such GPCR can include, for example, nanoantibodies. Thus, the RXFP agonist includes any agent with relaxin-like activity that is capable of binding to a relaxin receptor to elicit a relaxin-like response.

In one embodiment, relaxin peptide as used herein does not necessarily have to be 100% identical to human relaxin (e.g., H1, H2 and/or H3) but may be at least about 40%, 50%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the human relaxin peptide. Relaxin, as used herein, can be made by any method known to those skilled in the art.

Naturally occurring biologically active relaxin may be derived from human, murine (i.e., rat or mouse), porcine, or other mammalian sources. Also encompassed is relaxin modified to increase in vivo half life, e.g., PEGylated relaxin (i.e., relaxin conjugated to a polyethylene glycol), modifications of amino acids in relaxin that, for example, are subject to cleavage by degrading enzymes, and the like.

In one embodiment, RXFP agonists also encompasses relaxin, relaxin analogs, varients, and derivatives comprising a single chain, comprising A and B chains, or comprising A and B chains having N- and/or C-terminal truncations. In general, in H2 relaxin, the A chain can be varied from A(1-24) to A(10-24) and the B chain from B(1-33) to B(10-22); and in H1 relaxin, the A chain can be varied from A(1-24) to A(10-24) and the B chain from B(1-32) to B(10-22). Also included within the scope of relaxin, relaxin analogs and derivatives are other insertions, substitutions, or deletions of one or more amino acid residues, glycosylation variants, unglycosylated relaxin, organic and inorganic salts, covalently modified derivatives of relaxin, preprorelaxin, and prorelaxin.

Also encompassed is a relaxin analog having an amino acid sequence that differs from a wild-type (e.g., naturally-occurring) sequence with possible modifications to relaxin amino acid residues include acetylation, formylation or similar protection of free amino groups, including the N-terminal, amidation of C-terminal groups, or the formation of esters of hydroxyl or carboxylic groups, e.g., modification of the tryptophan (Trp) residue at B2 by addition of a formyl group. The formyl group is a typical example of a readily-removable protecting group.

Other possible modifications include replacement of one or more of the natural amino-acids in the B and/or A chains with a different amino acid (including the D-form of a natural amino-acid), including, but not limited to, replacement of the Met moiety at B24 with norleucine (Nle), valine (Val), alanine (Ala), glycine (Gly), serine (Ser), or homoserine (HomoSer). Other possible modifications include the deletion of a natural amino acid from the chain or the addition of one or more extra amino acids to the chain. Additional modifications include amino acid substitutions at the B/C and C/A junctions of prorelaxin, which modifications facilitate cleavage of the C chain from prorelaxin; and variant relaxin comprising a non-naturally occurring C peptide.

Examples of further chemical modifications that can be used in the invention include, but are not limited to, substitution of a D-amino acid for an L-amino acid, glycosylation of an amino acid side chain, alkylation of an amino acid side chain or N-terminus, acylation of an amino acid side chain or N-terminus, esterification of an amino acid side chain or C-terminus, phosphorylation of an amino acid side chain, sulfation of an amino acid side chain, and hydroxylation of an amino acid side chain.

Also encompassed are fusion polypeptides comprising relaxin and a heterologous polypeptide. A heterologous polypeptide (e.g., a non-relaxin polypeptide) fusion partner may be C-terminal or N-terminal to the relaxin portion of the fusion protein. Heterologous polypeptides include immunologically detectable polypeptides (e.g., "epitope tags," immunoglobulin); polypeptides capable of generating a detectable signal (e.g., green fluorescent protein, enzymes such as alkaline phosphatase, and others known in the art); therapeutic polypeptides, including, but not limited to, cytokines, chemokines, and growth factors. All such variations or alterations in the structure of the relaxin molecule resulting in variants are included within the scope of this invention so long as the functional (biological) activity of the relaxin is maintained. Preferably, any modification of relaxin amino acid sequence or structure is one that does not increase its immunogenicity in the individual being treated with the relaxin variant. Those variants of relaxin having the described functional activity can be readily identified using in vitro and in vivo assays known in the art.

In specific embodiments, RXFP agonists are low molecular weight, non-peptide, small molecules. Such compounds are often stable, easy to synthesize and adaptable for oral delivery. These small molecule RXFP1 agonists also have excellent absorption, distribution, metabolism, and excretion (ADME) properties. Although the small molecule RXFP agonists can bind to RXFP and activate the downstream signaling pathways, the small molecule cannot bind to the multiple orthosteric sites that the peptide ligand uses in the ectodomain and extracellular loops of the GPCR seven transmembrane domain (7TM). Some examples of small molecule RXFP1 agonists have been discussed in U.S. Pat. No. 10,125,112.

In one embodiment, the RXFP agonists are RXFP1 agonists. In a further embodiment, the RXFP agonists are RXFP1-specific agonists that are any agent capable of binding to RXFP1 to elicit a relaxin-like response.

In a preferred embodiment, the small molecule RXFP1 agonist is ML290 having a structure of

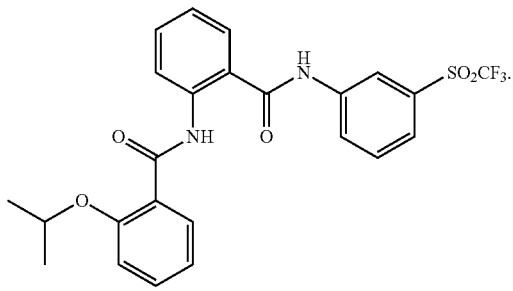

ML290 is >100-fold more selective towards RXFP1 over RXFP2 receptors and are able to increase cAMP levels and VEGF gene expression in THP1 cells. According to the subject invention, ML290 shows profound anti-calcification effects in primary human coronary artery smooth muscle cells cultured in osteogenic stimuli in vitro. In one embodiment, the small molecule RXFP1 agonists also encompass any related, active and low toxicity compounds produced based on the ML290 structure.

EGFR Inhibitors

Epidermal growth factors (EGFs) are signaling proteins that control a wide range of cellular functions critical for intercellular communication and tissue homeostasis. EGFR is a cell surface receptor with downstream receptor tyrosine kinase (RTK) activity, which binds multiple EGF ligands, and fibroblast growth factor 21 (FGF21), and has multiple functions that modulate vascular SMCs, cardiomyocytes, cardiac fibroblasts, endothelial cells (ECs), adipocytes, and immune cells.

EGFR and its ligands are expressed in the vascular system by, for example, SMCs and ECs, and can regulate their proliferation, migration, survival, and production of angiogenic factors and reactive oxygen species. Overexpression of EGFR promotes gene amplification and mutation consequence in cell proliferation, survival, invasion, metastasis, and tumor induced neoangiogenesis. EGFR and EGF signaling also promotes vascular abnormalities including abdominal aortic aneurysm formation, cardiac remodeling, endothelial dysfunction, fibrosis, hypertension, and neointimal hyperplasia.

EGFR inhibitors include, for example, the monoclonal antibodies (e.g., cetuximab, panitumumab, and matuzumab) that target the extracellular ligand-binding domain, and small-molecule tyrosine kinase inhibitors (e.g., vandetanib, osimertinib, gefitinib, erlotinib, lapatinib, and afatinib) that target intracellular domain.

In one embodiment, the inhibitor of EGFR can be, for example, necitumumab; saracatinib; canertinib; dacomitinib; vandetanib; neratinib; erlotinib; gefitinib; afatinib;

osimertinib; lapatinib; AG1478; AG490; CP724714; WZ4002; sapitinib; CUDC-101; PD153035; pelitinib; AEE788; AC480; OSI-420; WZ3146; Allitinib; Rociletinib; Varlitinib; Icotinib; TAK-285; WHI-P154; Daphnetin; PD168393; CNX-2006; Tyrphostin 9; AG-18; Epertinib; BI-4020; Tyrphostin AG-528; SU5214; RG 13022; TQB3804; TAS6417; Pyrotinib; PD153035; AG 494; AG 555; Theliatinib; Avitinib; Lazertinib; Lifirafenib; Nazartinib; Brigatinib; Tucatinib; AZD3759; CL-387785; Poziotinib; AZ5104; and Mobocertinib. Preferably, the inhibitor of EGFR is AG1478.

Formulation

In one embodiment, the subject invention provides compositions comprising one or more molecules/compounds selected from RXFP agonists and EGFR inhibitors according to the subject invention and a pharmaceutically acceptable carrier.

In specific embodiments, the composition of the subject invention comprises one or more RXFP agonists, preferably, RXFP1 agonists, and a pharmaceutically acceptable carrier. In a preferred embodiments, the composition of the subject invention comprises one or more low molecular weight, non-peptide, small molecule RXFP agonists, preferably, low molecular weight, non-peptide, small molecule RXFP1 agonists, and a pharmaceutically acceptable carrier.

In a specific embodiment, the composition of the subject invention comprises a therapeutically effective amount of ML290, and a pharmaceutically acceptable carrier.

In some embodiments, the composition may further comprise one or more EGFR inhibitors selected from necitumumab; saracatinib; canertinib; dacomitinib; vandetanib; neratinib; erlotinib; gefitinib; afatinib; osimertinib; lapatinib; AG1478; AG490; CP724714; WZ4002; sapitinib; CUDC-101; PD153035; pelitinib; AEE788; AC480; OSI-420; WZ3146; Allitinib; Rociletinib; Varlitinib; Icotinib; TAK-285; WHI-P154; Daphnetin; PD168393; CNX-2006; Tyrphostin 9; AG-18; Epertinib; BI-4020; Tyrphostin AG-528; SU5214; RG 13022; TQB3804; TAS6417; Pyrotinib; PD153035; AG 494; AG 555; Theliatinib; Avitinib; Lazertinib; Lifirafenib; Nazartinib; Brigatinib; Tucatinib; AZD3759; CL-387785; Poziotinib; AZ5104; and Mobocertinib.

In one embodiment, the compounds may be in a pharmaceutically acceptable salt form or a form of free base. Examples of pharmaceutically acceptable salts include, without limitation, the nontoxic inorganic and organic acid addition salts such as acetate, aconate, ascorbate, benzenesulfonate, benzoate, cinnamate, citrate, embonate, enantate, formate, fumarate, glutamate, glycolate, hydrochloride, hydrobromide, lactate, maleate, alonate, mandelate, methanesulfonate, naphthalene-2-sulphonate, nitrate, perchlorate, phosphate, phthalate, salicylate, sorbate, stearate, succinate, sulphate, tartrate, toluene-p-sulphonate, and the like.

Suitable acids for use in the preparation of pharmaceutically acceptable salts of a compound described herein, include, but are not limited to, aceptic acid; 2,2-dichoroacetic acid; acylated amino acids; adipic acid; alginic acid; ascorbic acid; L-aspartic acid; benzenesulfonic acid; benzoic acid; 4-acetamidobenzoic acid; boric acid; (+)-camphoric acid; camphorsulfonic acid; (+)-(1S)-camphor-10-sulfonic acid; capric acid; caproic acid; caprylic acid; cinnamic acid; citric acid; cyclamic acid; cyclohexanesulfamic acid; dodecylsulfuric acid; ethane-1,2-disulfonic acid; ethanesulfonic acid; 2-hydroxyethanesulfonic acid; formic acid; fumaric acid; galactaric acid; gentisic acid; glucoheptonic acid; D-gluconic acid; D-glucuronic acid; L-glutamic acid; α-oxo-glutaric acid; glycolic acid; hippuric acid; hydrobromic acid; hydrochloric acid; hydroiodic acid; (+)-L-lactic acid; (+/−)-DL-lactic acid; lactobionic acid; lauric acid; maleic acid; (−)-L-malic acid; malonic acid; (+/−)-DL-mandelic acid; methanesulfonic acid; naphthalene-2-sulfonic acid; naphthalene-1,5-disulfonic acid; 1-hydroxy-2-naphtoic acid; nicotinic acid; nitric acid; oleic acid; orotic acid; oxalic acid; palmitic acid; pamoic acid; perchloric acid; phosphoric acid; L-pyroglutamic acid; saccharic acid; salicyclic acid; 4-amino-salicylic acid; sebacic acid; stearic acid; succinic acid; sulfuric acid; tannic acid; (+)-L-tartaric acid; thiocyanic acid; p-toluenesulfonic acid; undecylenic acid; and valeric acid.

In one embodiment, the composition according to the subject invention also comprises a pharmaceutically acceptable carrier. "Pharmaceutically acceptable carrier" refers to a diluent, adjuvant or excipient with which the one or more active agents disclosed herein can be formulated. Typically, a "pharmaceutically acceptable carrier" is a substance that is non-toxic, biologically tolerable, and otherwise biologically suitable for administration to a subject, such as an inert substance, added to a pharmacological composition or otherwise used as a diluent, adjuvant or excipient to facilitate administration of the composition disclosed herein and that is compatible therewith.

Examples of carriers suitable for use in the pharmaceutical compositions are known in the art and such embodiments are within the purview of the invention. The pharmaceutically acceptable carriers and excipients, including, but not limited to, aqueous vehicles, water-miscible vehicles, non-aqueous vehicles, stabilizers, solubility enhancers, isotonic agents, buffering agents, suspending and dispersing agents, wetting or emulsifying agents, complexing agents, sequestering or chelating agents, cryoprotectants, lyoprotectants, thickening agents, pH adjusting agents, and inert gases. Other suitable excipients or carriers include, but are not limited to, dextran, glucose, maltose, sorbitol, xylitol, fructose, sucrose, and trehalose.

In one embodiment, the subject invention provides compounds and compositions comprising such compounds for treating, preventing or ameliorating excess or inappropriate vascular calcification, for example, medial vascular calcification or intimal atherosclerotic calcification.

In one embodiment, the molecules/compounds, and compositions comprising such molecules/compounds can be used for preventing, or reducing the formation of calcifying EVs and caveolae trafficking in vascular SMCs.

In one embodiment, the molecules/compounds, and compositions comprising such molecules/compounds can be used for reducing the risk of developing coronary artery disease in a subject (e.g., patients with diabetes, myocardial infarctions, chronic kidney disease, and metabolic syndrome).

In one embodiment, the molecules/compounds, and compositions comprising such molecules/compounds can be used for reducing the mineralizing properties of EVs in vascular SMCs, and for preventing or reducing mineral deposition in vascular wall.

The pharmaceutical composition is used for convenient and effective administration in effective amounts with a suitable pharmaceutically acceptable carrier in an acceptable dosage unit. In the case of compositions containing supplementary active ingredients, the dosages may be determined by reference to the usual dose and manner of administration of the said ingredients.

In one embodiment, aqueous suspensions contain one or more RXFP agonists, preferably, RXFP1 agonists, and/or EGFR inhibitors in admixture with excipients suitable for the manufacture of aqueous suspensions. Such excipients include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending one or more RXFP agonists, preferably, RXFP1 agonists, and/or EGFR inhibitors in a vegetable oil, such as *arachis* oil, olive oil, sesame oil or coconut oil, or in a mineral oil such as liquid paraffin. The oil suspensions can contain a thickening agent, such as beeswax, hard paraffin or cetyl alcohol. Sweetening agents can be added to provide a palatable oral preparation. These formulations can be preserved by the addition of an antioxidant such as ascorbic acid.

The pharmaceutical formulations of the subject invention can also be in the form of oil-in-water emulsions. The oily phase can be a vegetable oil, such as olive oil or *arachis* oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening and flavoring agents. Syrups and elixirs can be formulated with sweetening agents, such as glycerol, sorbitol or sucrose. Such formulations can also contain a demulcent, a preservative, a flavoring or a coloring agent.

In one embodiment, the pharmaceutical composition comprising one or more RXFP agonists, preferably, RXFP1 agonists, and/or EGFR inhibitors according to the invention, together with a conventional adjuvant, carrier, or diluent, may thus be placed into the form of solids including tablets, filled capsules, powder and pellet forms, and liquids such as aqueous or non-aqueous solutions, suspensions, emulsions, elixirs, and capsules filled with the same. The composition may further comprise conventional ingredients in conventional proportions, with or without additional active compounds.

In a further embodiment, the composition is in the powder form. The pharmaceutically accepted carrier is a finely divided solid, which is in a mixture with the finely divided active compounds. In another embodiment, the composition is in the tablet form. The active component is mixed with the pharmaceutically accepted carrier having the necessary binding capacity in suitable proportions and compacted in desired shape and size. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

In a further embodiment, the composition is in other solid forms including capsules, pills, cachets, and lozenges, which are suitable for oral administration.

In one embodiment, dispersible powders and granules suitable for preparation of an aqueous suspension by the addition of water can be formulated from RXFP agonists, preferably, RXFP1 agonists, and/or EGFR inhibitors in admixture with a dispersing, suspending and/or wetting agent, and one or more preservatives. Suitable dispersing or wetting agents and suspending agents are exemplified by those disclosed above.

In one embodiment, the composition is formulated in accordance with routine procedures as a pharmaceutical composition adapted for local administration to humans. Typically, compositions for local administration are solutions in a sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The pharmaceutical compositions may be formulated in any forms that are suitable for parenteral administration, including solutions, suspensions, emulsions, micelles, liposomes, microspheres, nanosystems, semi-solid, and solid forms suitable for solutions or suspensions in liquid prior to injection.

The formulations containing one or more RXFP agonists, preferably, RXFP1 agonists, and/or EGFR inhibitors be formulated for administration in any conventionally acceptable way including, but not limited to subcutaneously, intramuscularly, intravenously, sublingually, topically, orally and via inhalation.

Methods

In one embodiment, the subject invention provides a method for treating, preventing or ameliorating vascular calcification, for example, medial vascular calcification or intimal atherosclerotic calcification, via the activation of RXFP, preferably, RXFP1, the method comprising administering to a subject in need of such treatment, prevention or amelioration, a therapeutically effective amount of one or more RXFP agonists, preferably, RXFP1 agonists of the subject invention, and optionally, a pharmaceutically acceptable salt or solvate thereof. In one embodiment, the subject has been diagnosed with medial vascular calcification or intimal atherosclerotic calcification.

In one embodiment, the method for treating, preventing or ameliorating vascular calcification further comprises administering to the subject a therapeutically effective amount of one or more EGFR inhibitors, and optionally, a pharmaceutically acceptable salt or solvate thereof.

In one embodiment, the subject invention provides a method for treating, preventing or ameliorating vascular calcification, e.g., medial vascular calcification or intimal atherosclerotic calcification, the method comprising administering to a subject in need of such treatment, prevention or amelioration, a therapeutically effective amount of a pharmaceutical composition/formulation of the subject invention, preferably, the pharmaceutical composition/formulation comprising one or more RXFP agonists, preferably, RXFP1 agonists and a pharmaceutically acceptable carrier, and optionally, one or more EGFR inhibitors.

"Therapeutically effective" refers to the amount of pharmaceutically active compound/molecule according to the subject invention that will result in a measurable desired medical or clinical benefit to a patient, as compared to the patient's baseline status or to the status of an untreated or placebo-treated (e.g., not treated with the compound/molecule) subject.

The term "subject" or "patient," as used herein, describes an organism, including mammals such as primates. Mammalian species that can benefit from the disclosed methods of treatment include, but are not limited to, apes, chimpanzees, orangutans, humans, and monkeys; domesticated animals such as dogs, cats; live stocks such as horses, cattle, pigs, sheep, goats, and chickens; and other animals such as mice, rats, guinea pigs, and hamsters.

In one embodiment, the subject has been diagnosed with CKD, diabetes, ageing, hyperparathyroidism, hyperphosphatemia, a vitamin D disorder, a vitamin K disorder, osteoporosis, Kawasaki disease, arterial calcification due to deficiency of CD73 (ACDC), generalized arterial calcification of infancy (GACI), idiopathic basal ganglia calcification (IBGC), pseudoxanthoma elasticum (PXE), rheumatoid arthritis, Singleton-Merten syndrome, β-thalassemia, atherosclerosis, hyperlipidemia, hypertension, T2DM, ESRD, amputation, Marfan's Syndrome, congenital bicuspid valve, and/or rheumatic heart disease.

In one embodiment, the subject has not been diagnosed with, treated, or undergone a treatment simultaneously for inflammatory, autoimmune diseases, cancer, or metabolic disorders.

In one embodiment, images of a patient's vascular system could be obtained using virtual-histology intravascular ultrasound (VH-IVUS), and patients exhibiting early calcification could be identified therefrom. In one embodiment, a patient suffering from atherosclerotic calcification can be identified using a computed tomography (CT) scan. The CT scan can be used to calculate an Agatston score, a pseudo-continuous variable derived from plaque densities and their areas in all coronary arteries, for a patient. A patient with an Agatston score of 0 would have no coronary artery calcification. Preferably, the method of the subject invention is for use in treating atherosclerotic calcification in a patient with an Agatston score of at least 10, at least 20, at least 40, at least 60 or at least 80.

The terms "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being.

The term "prevention" or any grammatical variation thereof (e.g., prevent, preventing, etc.), as used herein, includes but is not limited to, at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). The term "prevention" may refer to avoiding, delaying, forestalling, or minimizing one or more unwanted features associated with a disease or disorder, and/or completely or almost completely preventing the development of a disease or disorder and its symptoms altogether. Prevention can further include, but does not require, absolute or complete prevention, meaning the disease or disorder may still develop at a later time and/or with a lesser severity than it would without preventative measures. Prevention can include reducing the severity of the onset of a disease or disorder, and/or inhibiting the progression thereof.

In one embodiment, the subject invention provides a method for treating or preventing a disease associated with vascular calcification via the activation of RXFP, preferably, the activation of RXFP1, the method comprising administering to a subject in need of such treatment or prevention a therapeutically effective amount of one or more molecules selected from RXFP agonists, preferably, RXFP1 agonists, and/or EGFR inhibitors of the subject invention, and optionally, a pharmaceutically acceptable salt or solvate thereof.

In one embodiment, the subject invention provides a method for treating or preventing a disease associated with vascular calcification, the method comprising administering to a subject in need of such treatment or prevention a therapeutically effective amount of a pharmaceutical composition/formulation of the subject invention, preferably, the pharmaceutical composition/formulation comprising one or more RXFP agonists, preferably, RXFP1 agonists, (and optionally, one or more EGFR inhibitors) and a pharmaceutically acceptable carrier.

The diseases associated with vascular calcification include, but are not limited to CKD, diabetes, ageing, hyperparathyroidism, hyperphosphatemia, a vitamin D disorder, a vitamin K disorder, osteoporosis, Kawasaki disease, ACDC, GACI, IBGC, PXE, rheumatoid arthritis, Singleton-Merten syndrome, β-thalassemia, atherosclerosis, hyperlipidemia, hypertension, T2DM, ESRD, amputation, Marfan's Syndrome, congenital bicuspid valve, myocardial infarctions, metabolic syndrome and rheumatic heart disease.

In one embodiment, the methods of the subject invention are for treating, preventing or ameliorating cardiovascular calcification via the activation of RXFP, preferably, RXFP1, the method comprising administering to a subject in need a therapeutically effective amount of one or more molecules selected from RXFP agonists, preferably, RXFP1 agonists, and optionally, one or more EGFR inhibitors of the subject invention, or a pharmaceutical composition/formulation of the subject invention comprising such molecule(s).

In one embodiment, the method is for treating, preventing or ameliorating Mönckeberg's arteriosclerosis, calcific atherosclerosis, calcific medial vasculopathy, elastocalcinosis, aalcific aortic valvular stenosis, portal vein calcification or calcific uremic arteriolopathy (CUA), the method comprising administering to a subject in need a therapeutically effective amount of one or more molecules selected from RXFP agonists, preferably, RXFP1 agonists, and EGFR inhibitors of the subject invention, or a pharmaceutical composition/formulation of the subject invention comprising such molecule(s). In preferred embodiments, the subject has been diagnosed with one or more of these conditions.

In one embodiment, the method of treating, preventing or ameliorating medial vascular calcification or intimal atherosclerotic calcification comprises administering to a subject in need of such treatment, prevention or amelioration, a therapeutically effective amount of one or more RXFP agonists, preferably, RXFP1 agonists, of the subject invention and a pharmaceutically acceptable salt or solvate thereof, or a pharmaceutical composition/formulation of the subject invention comprising such molecule(s).

In one embodiment, the subject invention also provides a method for preventing or reducing the formation of calcifying EVs and caveolae trafficking in vascular SMCs of a subject, the method comprising administering to the subject a therapeutically effective amount of one or more molecules selected from RXFP agonists, preferably, RXFP1 agonists, and EGFR inhibitors of the subject invention, or a pharmaceutical composition/formulation of the subject invention comprising such molecule(s). In a preferred embodiment, the subject has been diagnosed with CKD or arteriosclerosis.

In one embodiment, the subject invention provides a method for preventing or reducing the formation of calcifying EVs and caveolae trafficking in vascular SMCs, the method comprising contacting vascular SMCs with a therapeutically effective amount of one or more molecules selected from RXFP agonists, preferably, RXFP1 agonists, and EGFR inhibitors of the subject invention, or a pharmaceutical composition/formulation of the subject invention comprising such molecule(s), wherein vascular SMCs are obtained from a subject suffering from a disease associated with vascular calcification. In a preferred embodiment, the subject has been diagnosed with CKD or arteriosclerosis.

In one embodiment, the subject invention also provides a method for treating or reducing the risk of developing coronary artery disease, in particular, in patients with diabetes, myocardial infarctions, CKD, and metabolic syndrome, the method comprising administering to a subject in need of such prevention or reduction a therapeutically effective amount of one or more molecules selected from RXFP agonists, preferably, RXFP1 agonists, and EGFR inhibitors of the subject invention, or a pharmaceutical composition/formulation of the subject invention comprising such molecule(s). Preferably, the subject has been diagnosed with one of these conditions.

In one embodiment, the subject invention provides a method for reducing the mineralizing properties of EVs in a subject, the method comprising administering to the subject a therapeutically effective amount of one or more molecules selected from RXFP agonists, preferably, RXFP1 agonists, and EGFR inhibitors of the subject invention, or a pharmaceutical composition/formulation of the subject invention comprising such molecule(s).

In one embodiment, the subject invention provides a method for reducing the mineralizing properties of EVs in vascular SMCs, the method comprising contacting vascular SMCs with one or more molecules selected from RXFP agonists, preferably, RXFP1 agonists, and EGFR inhibitors of the subject invention, or a pharmaceutical composition/formulation of the subject invention comprising such molecule(s). In a specific embodiment, EVs have an average diameter of about 90 nm to 110 nm, or about 100 nm.

In one embodiment, the subject invention provides a method for preventing or reducing mineral nucleation and deposition in vascular wall, the method comprising administering to a subject in need a therapeutically effective amount of one or more molecules selected from RXFP agonists, preferably, RXFP1 agonists, and EGFR inhibitors of the subject invention, or a pharmaceutical composition/formulation of the subject invention comprising such molecule(s).

In one embodiment, the subject invention provides a method for preventing or reducing mineralization in the vascular system of a subject, the method comprising administering to the subject a therapeutically effective amount of one or more molecules selected from RXFP agonists, preferably, RXFP1 agonists, and EGFR inhibitors of the subject invention, or a pharmaceutical composition/formulation of the subject invention comprising such molecule(s).

In one embodiment, the subject invention provides a method for treating, preventing and reducing calcification of vascular SMCs, the method comprising administering to the subject in need a therapeutically effective amount of one or more molecules selected from RXFP agonists, preferably, RXFP1 agonists, and EGFR inhibitors of the subject invention, or a pharmaceutical composition/formulation of the subject invention comprising such molecule(s).

In specific embodiments, the subject invention provides methods for treating intimal atherosclerotic and/or medial CKD calcification in a subject diagnosed therewith, the method comprising administering to the subject in need a therapeutically effective amount of one or more RXFP agonists, preferably, RXFP1 agonists, of the subject invention, or a pharmaceutical composition/formulation of the subject invention comprising such molecule(s).

In a specific embodiment, the one or more RXFP agonists for use in the methods according to the subject invention are small molecule RXFP1 agonists. In a preferred embodiment, the small molecule RXFP1 agonist is ML290.

In certain embodiments, RXFP1 agonists contact vascular SMCs at a concentration ranging from about 1 nM to about 500 µM, from about 10 nM to about 400 µM, from about 20 nM to about 300 µM, from about 50 nM to about 200 µM, from about 100 nM to about 150 µM, from about 200 nM to about 100 µM, from about 500 nM to about 100 µM, from about 500 nM to about 50 µM, from about 1 µM to about 25 µM, or from about 1 µM to about 10 µM.

In some embodiments, the one or more EGFR inhibitors for use in the methods according to the subject invention are selected from necitumumab; saracatinib; canertinib; dacomitinib; vandetanib; neratinib; erlotinib; gefitinib; afatinib; osimertinib; lapatinib; AG1478; AG490; CP724714; WZ4002; sapitinib; CUDC-101; PD153035; pelitinib; AEE788; AC480; OSI-420; WZ3146; Allitinib; Rociletinib; Varlitinib; Icotinib; TAK-285; WHI-P154; Daphnetin; PD168393; CNX-2006; Tyrphostin 9; AG-18; Epertinib; BI-4020; Tyrphostin AG-528; SU5214; RG 13022; TQB3804; TAS6417; Pyrotinib; PD153035; AG 494; AG 555; Theliatinib; Avitinib; Lazertinib; Lifirafenib; Nazartinib; Brigatinib; Tucatinib; AZD3759; CL-387785; Poziotinib; AZ5104; and Mobocertinib. Preferably, the inhibitor of EGFR is AG1478.

In certain embodiments, EGFR inhibitors contact vascular SMCs at a concentration ranging from about 1 nM to about 500 LIM, from about 10 nM to about 400 µM, from about 20 nM to about 300 µM, from about 50 nM to about 200 µM, from about 100 nM to about 150 µM, from about 200 nM to about 100 µM, from about 500 nM to about 100 µM, from about 500 nM to about 50 µM, from about 1 µM to about 25 µM, or from about 1 µM to about 10 µM.

The compositions of the present invention can be administered to the subject being treated by standard routes, including the local, oral, ophthalmic, nasal, topical, transdermal, intra-articular, parenteral (e.g., intravenous, intraarterial, intraperitoneal, intrathecal, intraventricular, intradermal, intracavity, subcutaneous or intramuscular), intracranial, intracerebral, intraspinal, intrauterine, or rectal route. Depending on the condition being treated, one route may be preferred over others, which can be determined by those skilled in the art. Preferably, the composition is administered by injection (e.g., IV injection), gradual infusion over time or implantation.

Depending on the route of administration, the pharmaceutical composition can be associated with a material to protect the pharmaceutical composition from the action of enzymes, acids, and other natural conditions that may inactivate the pharmaceutical composition. Dispersions can also be prepared in glycerol, liquid polyethylene glycols, and mixtures thereof, and in oils. Under ordinary conditions of storage and use, these preparations may contain a preservative to prevent the growth of microorganisms.

Administration can be carried out using therapeutically effective amounts of the agents described herein for periods of time effective according to the subject invention. The effective amount may be determined by one of ordinary skill in the art and includes exemplary dosage amounts for a subject of from about 0.005 to about 500 mg/kg of body weight of active compound per day, which may be administered in a single dose or in the form of individual divided doses, such as from 1 to 4 times per day.

Alternatively, the dosage amount may be from about 0.01 to about 450 mg/kg of body weight of active compound per day, from about 0.05 to about 400 mg/kg of body weight of active compound per day, from about 0.1 to about 300 mg/kg of body weight of active compound per day, from about 0.1 to about 250 mg/kg of body weight of active compound per day, from about 0.2 to about 200 mg/kg of body weight of active compound per day, from about 0.5 to about 150 mg/kg of body weight of active compound per day, from about 0.5 to 100 mg/kg of body weight of active compound per day, from about 0.5 to about 75 mg/kg of body weight of active compound per day, from about 0.5 to about 50 mg/kg of body weight of active compound per day, from about 0.5 to about 25 mg/kg of body weight of active compound per day, from about 1 to about 20 mg/kg of body weight of active compound per day, from about 1 to about 15 mg/kg of body weight of active compound per day, from about 1 to about 10 mg/kg of body weight of active compound per day.

In specific embodiments, the dosage amount may be about 500 mg/kg of body weight of active compound per day, about 400 mg/kg of body weight of active compound per day, about 300 mg/kg of body weight of active compound per day, about 200 mg/kg of body weight of active compound per day, about 100 mg/kg of body weight of active compound per day, about 50 mg/kg of body weight of active compound per day, 20 mg/kg of body weight of active compound per day, about 10 mg/kg of body weight of active compound per day, about 5 mg/kg of body weight of active compound per day, about 1 mg/kg of body weight of active compound per day, about 0.5 mg/kg of body weight of active compound per day, or about 0.1 mg/kg of body weight of active compound per day.

In specific embodiments, the composition of the subject invention may be administered at least once a day, twice a day, or three times a day for consecutive days, e.g. 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. The composition of the subject invention may also be administered for weeks, months or years.

As used herein, the reduction or delay in onset, incidence or severity according to the method of the subject invention can be about a 5%, 10%, 15%, 20%, 25%, 30%, 40%, 50%, 60%, 70%, 80%, 90%, 100%%, or any amount of reduction in between.

In one embodiment, the method according to the subject invention further comprises a step of evaluating the treatment or reduction in response to one or more RXFP agonists, preferably, RXFP1 agonists, and/or EGFR inhibitors or the pharmaceutical composition of the subject invention.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., subranges within the disclosed range), specific embodiments therein are intended to be explicitly included.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

EXAMPLES

Example 1—the Role of SMC Caveolin-1 in CKD Mineralization

Causal mechanisms associated with EV-based mineralization are difficult to study in vivo. To demonstrate the relevance of caveolin-1 in SMC-driven calcification in vivo, tamoxifen-inducible SMC-specific caveolin-1 deficient mice (SMMHC-CreER$^{T2+}$/Cav1$^{\Delta/\Delta}$) fed an adenine and high phosphate diet were used to induce CKD, to disrupt calcifying EV formation in vivo and to assess the effects on SMC-driven medial calcification in the context of CKD.

The mechanistic studies that alter EV formation in vivo and show changes to mineral formation in the vascular wall demonstrated the degree to which these EVs participate in calcification. The data suggest a role for caveolin-1 in the formation of calcifying EVs and SMC-driven calcification.

Eight-week old SMMHC-CreER$^{T2+}$/Cav1$^{fl/fl}$ mice receive daily intraperitoneal injections of either peanut oil (vehicle control) or tamoxifen (1 mg/kg) for two weeks. Following the final injection, mice receive an adenine-enriched (0.2%) diet for 6 weeks to induce kidney dysfunction. Elevated phosphate (1.8%) is then added to the diet to induce medial calcification. Using a sensitive near-infrared calcium mineral tracer (OsteoSense 680), significant aortic calcification in mice was observed after 2 weeks of the high phosphate diet (FIG. 1). Vascular calcification continues to increase for up to 6 weeks of the high phosphate diet.

To trace the growth of vascular calcification, the temporal information on calcification growth in a single mouse was compared by using calcium mineral-binding dyes with different fluorescent properties injected at different time points. The high phosphate diet was continued for 6 weeks. The longitudinal tracing was performed using calcein green injected into atherosclerotic Apoe−/− mice after 8 weeks on an atherogenic diet and alizarin red S in the same mice 3 weeks later. Imaging green and red fluorescence provided snapshots of aortic calcification at 8 and 11 weeks, respectively (FIG. 2A). Observations within histological sections revealed green calcifications in Apoe−/− mice after 8 weeks on an atherogenic diet embedded within alizarin red stained larger calcifications that were formed 3 weeks later (FIG. 2B). The custom edge detection algorithms localize and quantify the areas of the two fluorescent signals (FIG. 2C).

Similar techniques were used to trace calcium mineral formation in the CKD model at 2 (calcein green injection) and 4 weeks (alizarin red injection) of the high phosphate diet. A final injection of OsteoSense 680 at week 6 can determine the final calcification burden by scanning the entire aorta using a LI-COR Odyssey CLx imaging system, as shown in FIG. 1.

In addition to fluorescent tracing of vascular mineral, the histopathological assessment of phenotypic markers associated with calcification (e.g., TNAP, Runx2, osteocalcin), von Kossa staining of phosphate-based minerals in histological sections and assessment of serum factors indicative of kidney dysfunction and calcification are performed. Based upon the OsteoSense fluorescence signal from the CKD studies (n=5, 194.2±82.6), these studies require 16 mice per group to observe a 33% minimum change (two-tailed test) with 80% power and 95% confidence.

Mice were divided into four groups: 1) vehicle control mice injected with peanut oil fed the CKD diet regimen; 2) tamoxifen treated mice to delete SMC caveolin-1 fed the CKD diet regimen; 3) vehicle control mice injected with peanut oil fed a chow diet; and 4) tamoxifen treated mice to delete SMC caveolin-1 fed a chow diet. The latter two groups are used to establish signal fluorescence baselines for each group.

The mineral tracing shows an increase in calcification over the 6-week high phosphate diet in the CKD groups. Given the requirement for caveolin-1 in SMC mineralization in vitro, mice without SMC caveolin-1 exhibit diminished vascular calcification compared to wild-type mice fed the CKD diet regimen. No calcification is seen in the chow fed mice.

Alternatively, SMCs can be isolated from the aortae of these mice to explore altered caveolae structure and EV formation. In this case, the global caveolin-1 deficient mice (B6.Cg-Cav1$^{tm1Mls}$/J) can be used for comparison of mineralization potential and calcifying EV formation.

Example 2—Calcifying EVs Form and Derive Lipid Properties from SMC Caveolae

EVs released in pro-calcific conditions have physicochemical properties derived from SMC caveolae. The lipid content of EVs and SMC caveolae is compared. The size and charge properties of calcifying EVs and SMC caveolae are assessed.

Calcifying EVs build mineral in atherosclerotic plaques, and calcifying EV formation requires the presence of caveolin-1. Negatively charged phosphatidylserine increases the rate of mineral formation by immobilizing calcium ions on the membrane of calcifying EVs.

Phosphatidylserine plays a critical role in caveolae formation and trafficking. Calcifying EVs derive from caveolae, providing a phospholipid composition that aids in mineral formation.

Mass spectrometry is used to compare the lipidomic profiles of EVs isolated from the aortae of the four mouse groups discussed above. The EVs are extracted after 2 weeks of the high phosphate diet, when medial calcification has begun but before gross calcification may hinder the EV isolation procedures. The lipid makeup of these tissue-isolated EVs is compared to EVs and caveolae-enriched plasma membrane from SMCs cultured in pro-calcific conditions in vitro.

To obtain EVs from the mouse aortae, following collagenase digestion and tissue homogenization using a Dounce homogenizer, cells and large extracellular aggregates are removed by centrifugation steps of 1,000×g and 10,000×g, respectively. EVs are isolated from the remaining supernatant by ultracentrifugation at 100,000×g. Western blotting analyses of commonly enriched EV markers determine the efficacy of the isolation procedures. The presence of caveolin-1 and activity of the pro-calcific enzyme TNAP are also assessed in the extracted EVs.

To yield sufficient EVs for the protein analyses and the lipidomic and physical analyses, extracts are pooled from the aortae of three mice per group. All analyses are performed from five sets of pooled samples (n=5, 15 mice required per group).

The tissue extracted EVs are compared to EVs and caveolae membrane isolated from four different in vitro groups: 1) static SMCs cultured in control media; 2) static SMCs cultured in pro-calcific media; 3) SMCs exposed to cyclic 10% mechanical strain in control media; and 4) SMCs exposed to cyclic 10% mechanical strain for pro-calcific media.

Caveolae are known mechanosensors that rapidly assemble and disassemble in response to sudden changes in plasma membrane tension, but the effects of mechanical stimulation on calcifying EV formation have not been reported.

Given that the arterial wall experiences cyclic stretch over the course of the cardiac cycle, SMCs are exposed to varying levels of mechanical stimulation in culture using a Flexcell 5000XT to assess changes in EV formation. Compared to non-stretched controls (FIG. 3A), exposing SMCs to cyclic 10% strain for 72 h resulted in a redistribution of caveolin-1 from the membrane to the SMC cytoplasm (FIG. 3B). Cyclic stretch also led to an increase in caveolin-1 release into EVs in a dose dependent manner from 0 to 15% strain (FIG. 3C). The high variability for the 15% strain condition likely resulted from poor SMC viability in some samples at this high strain magnitude. Caveolae endocytosis is controlled by the enzyme dynamin. Inhibition of dynamin prevented the strain-induced increase in EV caveolin-1 (FIG. 3D), suggesting that these EVs derive from caveolae endocytosis.

Pro-calcific media, optimized to induce calcification, consists of growth media supplemented with 10 nM dexamethasone, 100 µM L-ascorbic acid, and 10 mM β-glycerolphosphate. All in vitro experiments proceed for 14 days, when release of calcifying EVs from human coronary artery SMCs in pro-calcific media peaks.

The inclusion of the mechanically stimulated culture provides two advantages. First, the addition of cyclic strain provides a more physiologically relevant culture environment than static tissue culture plastic. Second, the results show that cyclic mechanical stretch leads to increased elaboration of caveolin-1-positive EVs from SMCs (FIG. 3). The result shows elevated caveolin-1 release in EVs due to 10% strain without obvious deleterious effects to SMC viability. Therefore, cyclic (1 Hz) 10% strain is used in the subject studies.

EVs from the in vitro samples are isolated using previously established procedures, which includes 1,000×g and 10,000×g centrifugations to remove cells and large contaminants and a 100,000×g ultracentrifugation to obtain EVs suspended in conditioned media.

Caveolae-enriched membrane fractions can be obtained from SMCs at the study endpoints using a gradient-based (OptiPrep) centrifugation approach. Caveolae enrichment can be confirmed by western blotting for caveolin-1.

To ensure that measured effects are due to caveolae, methyl-β-cyclodextrin is used to disrupt caveolae (but preserve caveolin-1) and siRNA-mediated knockdown of caveolin-1 is performed for 24 h prior to EV collection for each culture condition.

Example 3—Lipidomic Analyses of EVs and Caveolae-Enriched Membrane

A mass spectrometry lipidomics workflow is used to compare the tissue isolated EVs, in vitro derived EVs, and SMC caveolae. Lipid content of isolated EVs and caveolae are extracted using an established methyl-tert-butyl ether (MTBE) protocol. The extracted lipids are then analyzed using liquid chromatography coupled to trapped ion mobility spectrometry-mass spectrometry (LC-TIMS-MS). LC-TIMS-MS separates lipids in three dimensions: retention time (LC), ion mobility (TIMS) and mass-to-charge ratios (m/z, MS). Lipids group into typical retention time and ion mobility windows. Their identity can then be obtained from their measured m/z using database searches (LIPID MAPS Lipidomics Gateway database, Simlipid (PREMIER Biosoft) and Metaboscape (Bruker)).

MS-based quantitation is performed using the addition of internal standards before the lipid extraction. The added internal standard is made up of a mixture of deuterated lipids from various lipid classes at precisely known concentrations (EquiSPLASH from Avanti Polar Lipids). Internal mass and ion mobility calibrations are performed by post-column introduction of calibration standards at the beginning and at the end of each run. The results indicated distinct lipid profiles in EV samples (FIG. 4, EVs isolated from a pro-calcific sample and a control sample).

To identify the lipid species, lipid database identifications is used within a mass accuracy window of ±3 ppm. The results show lipid class separation in the LC-TIMS domain (FIG. 4A), mass spectra (FIG. 4B), and lipid identifications with the sum compositions for each sample. Differences between the two samples were observed (FIG. 4C). A Levenshtein distance method, wherein identified lipid components are ranked by abundance for each sample, is used to quantify the similarity between samples. This method avoids complications arising from sample origin and differences in absolute lipid species abundance. Rather, similarities between samples are determined by how much the lipid ranking order of one sample must be modified to achieve the same ranking order of another sample.

Moreover, physical characterizations of EVs and SMC caveolae are assessed, e.g., the size and charge properties of EVs isolated from the tissues and cell culture conditions discussed above. These analyses enable the determination of the physical attributes associated with lipid differences observed in the mass spectrometry data. A portion of the collected samples containing EVs can be used for charge analysis by using a multifunctional nanopipette technique. The nanopipette has both a nanopore and nanoelectrode at the apex (FIG. 5A). Magnitude and frequency of collisions in the nanopore provide size and concentration data, and EV-induced potential changes at the nanoelectrode provide surface charge data. The close association of these features allows simultaneous EV-by-EV measurements. FIG. 5B shows data from EVs obtained from SMCs cultured under 10% cyclic stretch. Current spikes (black color trace), corresponding potential (red color trace), and first derivative of potential (blue color trace) demonstrate translocation of individual EVs through the nanopore. EVs (n=429) from stretched samples exhibit a higher potential, indicative of more negative charge, compared to EVs from non-stretched SMCs (n=386) (FIG. 5C).

Live SMCs from which the EVs are obtained are imaged using scanning ion conductance microscopy (SICM) to determine changes in the SMC plasma membrane in conditions associated with changes in EV composition (lipids and caveolin-1). SICM, a unique combination of patch-clamp and SPM techniques, has emerged as a powerful and versatile tool for high spatial resolution imaging and analysis of live cells.

The SICM imaging system is integrated with a dual-barrel nanopipette to acquire both topography and surface charge/surface potential images of live cells. High resolution SICM (~50 nm spatial resolution) is performed on various types of live cells, including Hela cell, HEK, fibroblast, and cardiomyocytes. Topography and surface potential images can be simultaneously acquired. The images can help to identity transmembrane pore structures on the cell membrane. This technique is used with the topography analyses to identify caveolae, which have a diameter of about 60-80 nm. The fluorescence microscopy is integrated to correlate the location of caveolae domains on the SMC plasma membrane. Also, the capability of SICM to image EVs immobilized is tested on a surface to compare to the nanopipette analyses.

EVs with more pro-calcific potential (high caveolin-1 and TNAP) will be most like SMC caveolae, indicative of the caveolar origin of these EVs. Specifically, the lipid profile of EVs isolated from vehicle-injected CKD mouse aortae most closely matches EVs from pro-calcific, stretched SMCs and SMC caveolae. The lipids associated with the calcifying EVs may provide a negative charge.

The unbiased lipidomics approach provide valuable new knowledge in calcifying EV phospholipid content, and the approaches have been validated. If the phospholipid profiles observed in the pro-calcific samples do not significantly differ from the control samples, it could be due to a relatively low contribution of calcifying EVs to the total EV lipid profile (i.e., poor signal-to-noise). If this is observed, a density-based ultracentrifugation approach is used to enrich calcifying EVs. Relative enrichment can be assessed by measuring TNAP before and after ultracentrifugation. No observations of phospholipid changes following calcifying EV enrichment indicate that, though calcifying EV formation requires caveolin-1,6, caveolae do not directly form the EV structure. As an additional assessment of the role of caveolae in calcifying EV formation, other caveolar scaffolding proteins are assayed in calcifying EVs (e.g., cavin1). If differences are observed between in vivo groups but the tissue isolated EVs do not correlate with EVs from SMC cultures, different media formulations may be used to induce in vitro mineralization and/or use mouse SMC cultures to explore species differences.

Example 4—Caveolae-Derived EV Properties Accelerate Mineralization

Computational and in vitro platforms are used to show that the caveolae-derived EV properties contribute to EV mineralization. The computational simulations are compared to experimental observations of mineralization using the 3-D collagen hydrogel platform that enables the study of mineral formation in calcifying EVs. Calcific mineral grows and matures within the hydrogel over the course of 7 days with a spectroscopic signature similar to microcalcifications in human atherosclerotic plaques. This platform is used to assess the localization of mineral formation within calcifying EVs and changes in EV calcification potential due to caveolae disruption.

With the updated phospholipid compositions of the calcifying EVs obtained, a simulation systems consisting of the lipid bilayer and the pre-nucleation clusters for both $Ca^{2+}$—$HPO_4^{2-}$ and $Ca^{2+}$—$PO_4^{3-}$ is set up. For detailed investigations of phospholipid interactions and $Ca^{2+}$—$HPO_4^{2-}$ or $Ca^{2+}$—$PO_4^{3-}$, all-atom simulations using the NAMD 2.13 molecular simulation package and CHARMM36m force-field are used. For the $Ca^{2+}$—$PO_4^{3-}$ aggregation and crystallization in the EVs, coarse-grained simulations using Gromacs simulation package with Martini force-field are used. The coarse-grained model has been tested for building various EV systems that are stable and allow crystal formation.

The scope and study the crystal growth are expended with continuous addition of ions to better simulate the in vivo situation. Simulations will be stopped at regular intervals and ions will be added to the system followed by re-running of the updated system.

To experimentally assess mineral formation within EVs, a collagen hydrogel platform is used. The hydrogels are made by slowly raising the pH of collagen dissolved in acetic acid to 7-8, causing the collagen to form a fiber network. EVs from the in vitro groups described above will be added to collagen hydrogels and incubated at 37° C. for up to 7 days. This allows the visualization of the mineral formation directly from the EVs. Overall differences in mineralization can be measured using a fluorescence-based probe (OsteoImage, Lonza) for in vitro models of EV-mediated calcification. In separate collagen hydrogels, a near-infrared calcium mineral tracer (OsteoSense) is used to image and quantify the size distribution of calcifications within the collagen hydrogels (FIG. 6).

These analyses are performed after 2, 4, and 7 days of EV incubation in the collagen hydrogels. To localize the mineral formation within EVs, collagenase is used to dissociate the hydrogels at these time points. The liberated EVs are drop-cast on a transmission electron microscopy (TEM) grid on a glass slide.

The computational studies provide insight into the mechanisms of mineral nucleation and growth and would fill knowledge gaps in both physiological and pathological mineralization. Specifically, computations will elucidate how Ca2+-PO43- molecular clusters are formed along the EV membrane. Compared to EVs from SMCs cultured in pro-calcific media and subjected to mechanical stimulation, it is expected to observe minimal calcific mineral formation in control samples and samples with caveolae disruption by methyl-β-cyclodextrin or siRNA-mediated knockdown of caveolin-1.

Figures 7A, 7B:
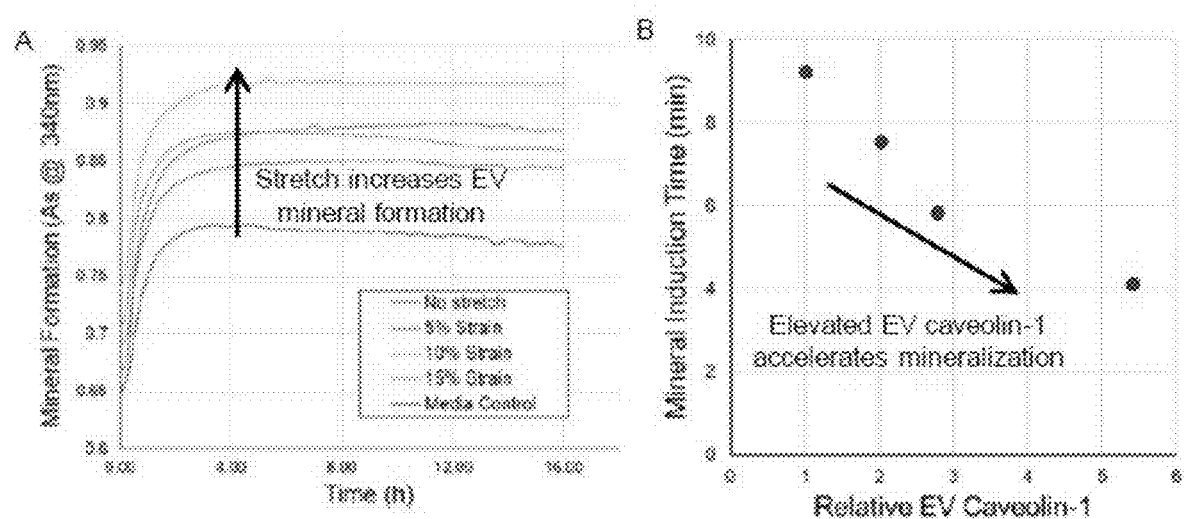
FIGS. 7A-7B show that A) Increased mineral formation is observed in EVs from SMCs exposed to cyclic stretch for 3 days compared to non-stretched controls. B) The mineralization potential, as shown by a decrease in the time required to induce mineralization in vitro, increases as EV caveolin-1 increases (measured by western blotting).

An assay originally developed to study mineral formation from growth plate cartilage EVs is performed to determine changes in mineralization potential associated with increased EV caveolin-1. The formation of calcium phosphate mineral leads to increased scattering of 340 nm light, which manifests as increased absorbance of the assay solution containing EVs. The results show a strain magnitude-dependent increase in mineral formation by EVs compared to a media control with no EVs (FIG. 7A). The mineralization potential of the EVs can be measured by the time at which rapid mineralization begins in this assay. EVs with higher mineralization potential mineralize more rapidly, as indicated by an earlier mineral induction time. Elevated EV caveolin-1 associated with increased mineralization potential in our preliminary analyses (FIG. 7B). These results further support the critical role for caveolae in calcifying EV formation.

TEM shows that collagen fibrils can initiate the mineralization that spread out from the contact point and grow along the superhelix of collagen fibrils. In addition to the single EV studies used above, molecular simulations can be used to investigate the EV crystal growth and interactions with collagen fibrils using all-atom simulations. Negatively charged groups in collagen fibrils can serve as the binding sites for Ca2+ and induce the oriented nucleation of apatite. The triple-helix structure of human collagen (pdb id: 6A0A) can be used with various forms of $Ca^{2+}$—$PO_4^{3-}$ clusters such as in the amorphous calcium phosphate precursor phase and in the octacalcium phosphate phase.

The results show that calcifying EVs originate from caveolae domains of SMCs. SMC caveolin-1 is required for calcification in a model of medial calcification. EVs liberated from SMCs in pro-calcific conditions contain similar lipid profiles to SMC caveolae. The caveolae-derived properties of calcifying EVs promote mineral formation.

Example 5—EGFR Inhibitor and RXFP1 Agonist to Treat CKD-Associated Vascular Calcification Because caveolae are critical for calcifying EV formation, modulation of caveolae trafficking for therapeutic benefit can be done with, for example, a known caveolin-1 interactor and a novel target.

Epidermal Growth Factor Receptor (EGFR) interacts with caveolin-1 and influences caveolae trafficking. EGFR tyrosine kinase inhibition (AG1478) prevents calcific mineral formation by SMCs in vitro (FIG. 8A) and reduces activity of tissue non-specific alkaline phosphatase (TNAP), a mineral promoting enzyme, in EVs (FIG. 8B).

EGFR activity influences caveolin-1 trafficking. EGFR activation results in dynamin-mediated cleavage and internalization of caveolae into cells. AG 1478 reduces dynamin activity and stabilizes EGFR-caveolae interactions in the plasma membrane. Thus, reducing caveolae internalization through EGFR inhibition can prevent formation of calcifying EVs. Treating SMCs with AG1478 does not change intracellular caveolin-1 (FIG. 8C) but reduces caveolin-1 released in EVs under pro-calcific conditions (FIG. 8D). EGFR inhibition is used clinically in cancer therapies. The demonstrated efficacy and relative safety of small molecule therapeutics indicate the potential for targeting EGFR for cardiovascular-related indications, such as vascular calcification.

Figure 9B:
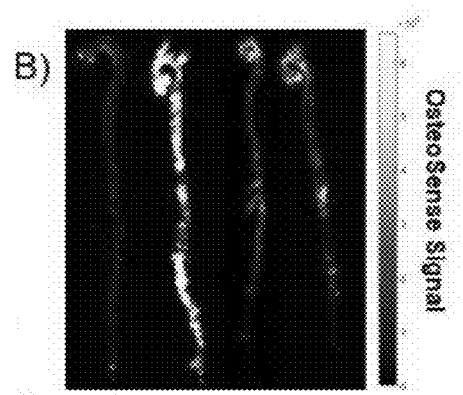
Figures 9C, 9D:
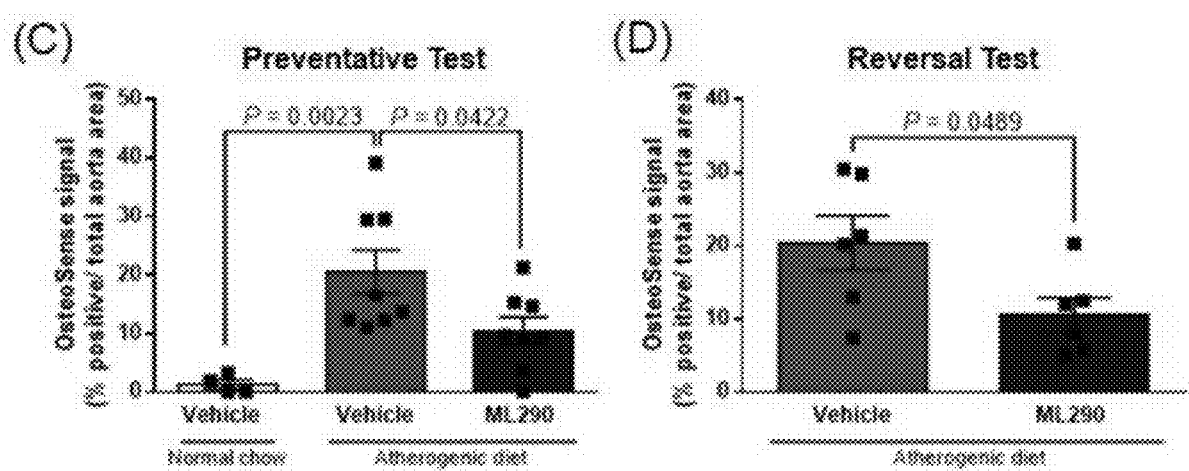

Relaxin Family Peptide Receptor 1 (RXFP1) agonism induces vasodilation through a mechanism that may involve interactions with endothelial nitric oxide synthase within caveolae. The relaxin peptide, activating RXFP1, has therapeutic potential in treating fibrosis and vasculopathies. Relaxin is safe and well-tolerated in humans, but peptide-based therapies for chronic diseases are limited by no oral bioavailability and low stability in vivo. ML290 is a potent and efficacious non-peptide agonist of human RXFP1. This small molecule utilizes allosteric sites on RXFP1 and does not interfere with natural hormone action. ML290 mitigates calcification of human SMCs in vitro and in atherosclerotic apolipoprotein E-deficient mice (FIG. 9). The myriad of cells responsible for remodeling in atherosclerosis does not allow us to directly connect these in vivo observations with the reduction in SMC-mediated calcification observed in vitro.

To test the therapeutic efficacy of these small molecules, e.g., ML290 or AG1478, the same CKD diet regimen is used as discussed above. A mouse model designed to test agonists for human RXFP1 is utilized. Since ML290 is a specific agonist for human RXFP1 and does not activate rodent receptor, hRXFP1/hRXFP1 mice have been created to test the therapeutic potential of ML290 in vivo.

Figure 10:
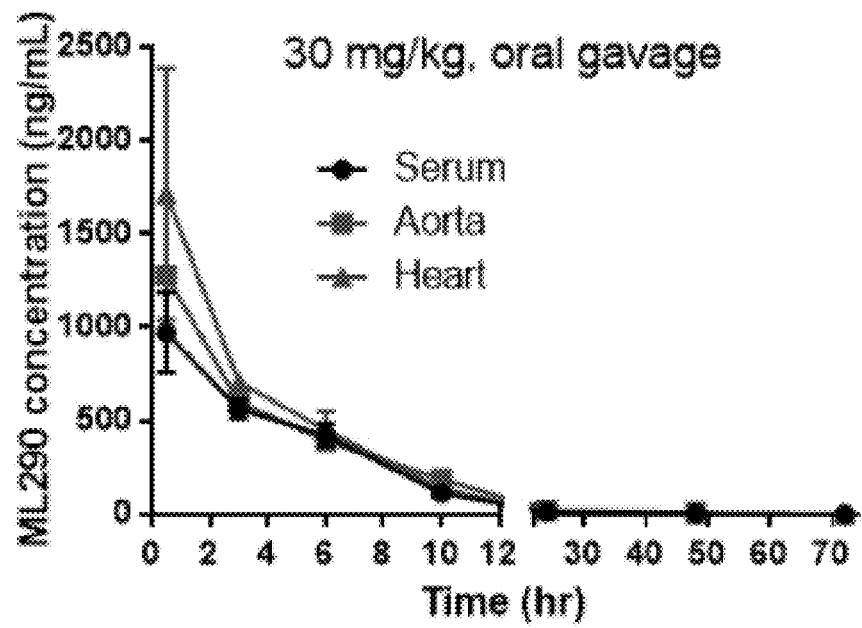
FIG. 10 shows ML290 bioavailability data.
Figure 11:
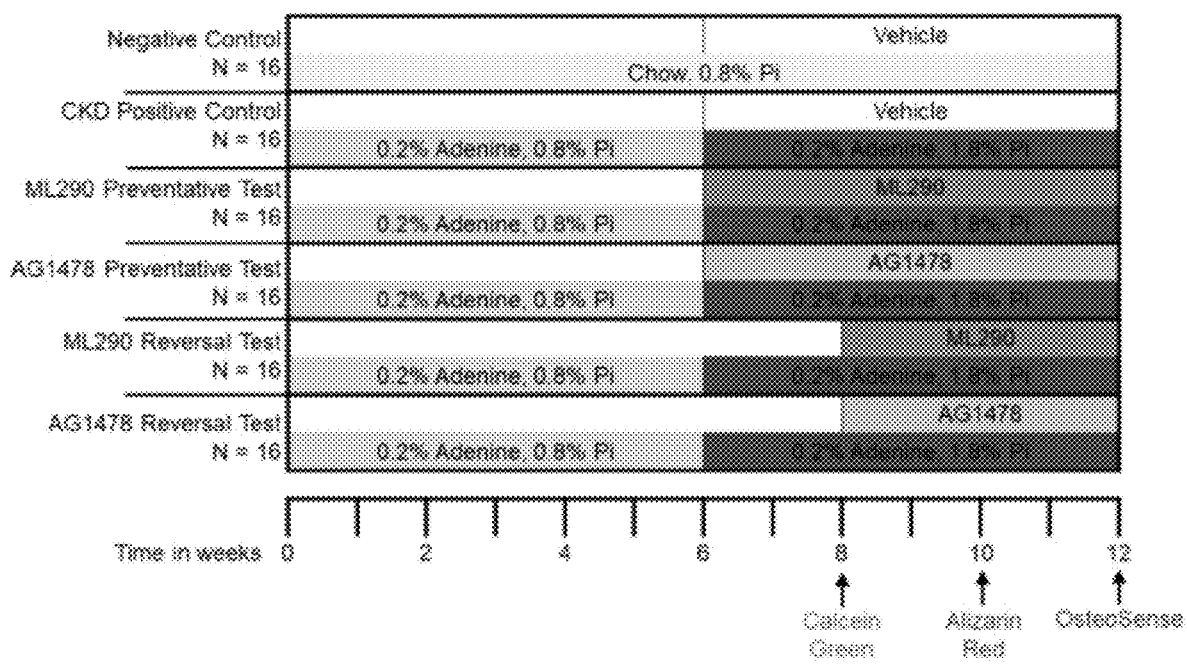
FIG. 11 shows the feeding and treatment schedule.

Pharmacokinetics study of ML290 (30 mg/kg) via oral administration in these mice indicated excellent stability of the compound in serum ($t\frac{1}{2}$=11 hr), heart ($t\frac{1}{2}$=T3 hr) and aorta ($t\frac{1}{2}$=8 hr) (FIG. 10). No adverse events have been observed in mice treated with ML290 via oral gavage in our preliminary 25-week atherosclerotic study (FIG. 9). Beginning at prescribed time points (FIG. 11), mice are treated with the EGFR inhibitor, AG1478 (20 mg/kg), or ML290 (30 mg/kg) via oral gavage every 2 days. Control mice receive vehicle gavage. The treatments begin either at the initiation of the high phosphate diet (to determine if the treatments prevent mineral formation) or after two weeks of the high phosphate diet (to determine if the treatments can reverse medial calcification).

Similar to the procedures performed on the SMMHC-CreER$^{T2+}$/Cav1$^{\Delta/\Delta}$ mice, calcein green is injected after 2 weeks of the high phosphate diet and alizarin red S is injected after 4 weeks of the high phosphate diet to provide snapshots of the existing mineral at these time points. An injection of OsteoSense 680 at the end of the 6-week high phosphate diet is used to determine the final calcification burden.

Figure 12:
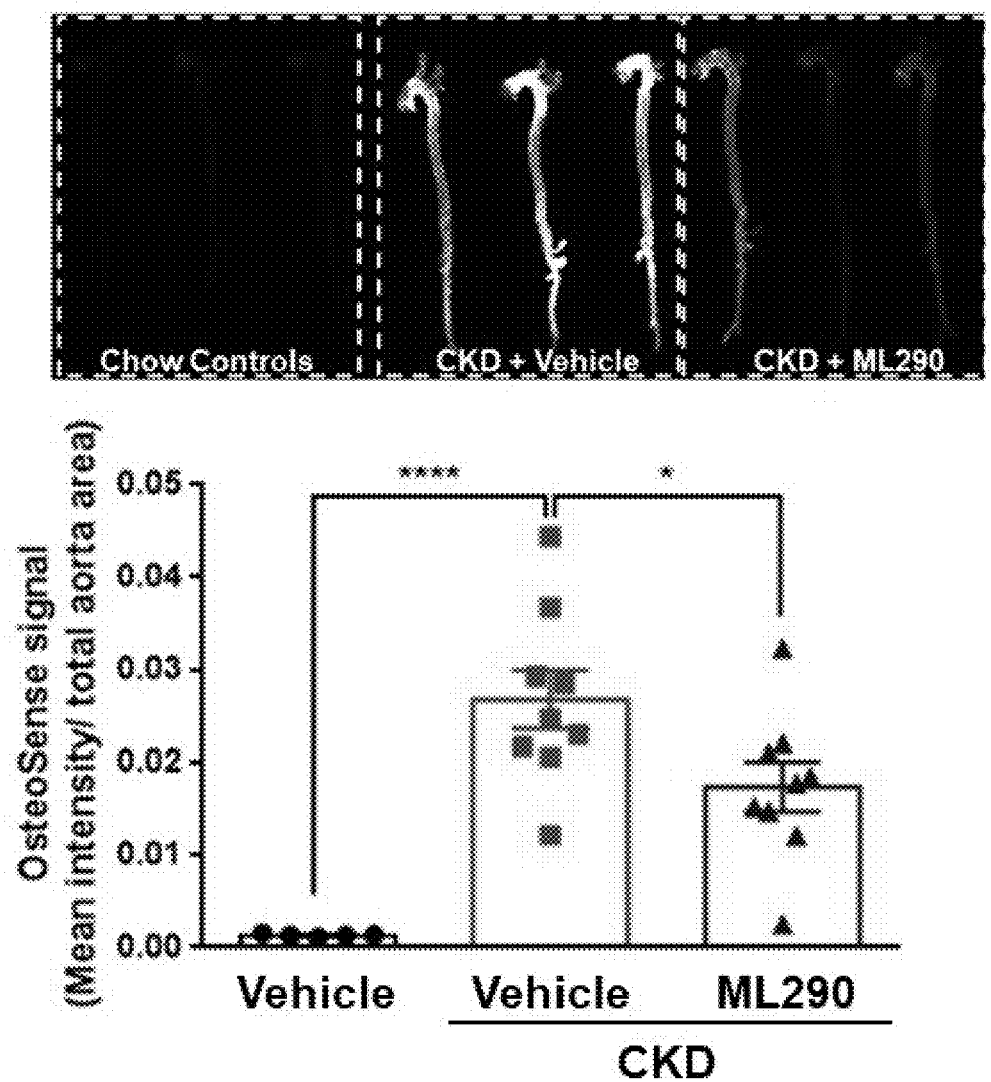
FIG. 12 shows that ML290 (30 mg/kg oral gavage) significantly prevents aortic calcification in CKD mice fed a high phosphate diet for 2 weeks. n=8 mice per group. ****p<0.001, *p=0.03.

To demonstrate the potential of ML290 for preventing calcification in the CKD model, an initial set of experiments is performed, wherein mice were treated with ML290 oral gavage at the initiation of the high phosphate diet. ML290 significant prevented aortic calcification (FIG. 12).

These analyses are extended to 6 weeks of the high phosphate diet, which has been shown to induce further calcific remodeling and allow the assessment of the reversibility of mineral deposition by the therapeutics. In addition to fluorescent tracing of vascular mineral, histopathological assessment of phenotypic markers (e.g., TNAP, Runx2, osteocalcin) associated with calcification and von Kossa staining of phosphate-based minerals in histological sections and assessment of serum factors indicative of kidney dysfunction and calcification are also performed. Based upon the OsteoSense fluorescence signal from CKD studies (n=5, 194.2±82.6), these studies require 16 mice per group to observe a 33% minimum change (two-tailed test) with 80% power and 95% confidence.

Six groups of mice are used to complete this study (FIG. 11): 1) mice fed a normal chow diet for 12 weeks (negative control); 2) mice fed the 12-week CKD regimen with drug vehicle started at the initiation of the high phosphate diet (positive control); 3) mice fed the 12-week CKD regimen with AG 1478 treatment starting at the onset of the high phosphate diet (preventative test); 4) mice fed the 12-week CKD regimen with ML290 treatment starting at the onset of the high phosphate diet (preventative test); 5) mice fed the 12-week CKD regimen with AG 1478 treatment starting after 2 weeks of the high phosphate diet (reversal test); and 6) mice fed the 12-week CKD regimen with ML290 treatment starting after 2 weeks of the high phosphate diet (reversal test).

EVs are isolated from the aortae of mice treated with AG1478 and ML290 to complete lipidomic and charge/size characterization studies. These analyses use the first 4 groups above, sacrificing the mice after 2 weeks of the high phosphate diet. This allows the assessment of the effect of the treatments on EV characteristics associated with mineral formation. Mass spectrometry-based lipidomic analyses and nanopipette measurements of EV size and charge allow the correlation of EV characteristics and the presence of mineral measured by the fluorescent tracers. Extracts are pooled from the aortae of three mice per group, and all analyses are performed from five sets of pooled samples (n=5, 15 mice required per group).

The in vitro data show that EGFR inhibition and RXFP1 agonism can directly affect the calcification potential of SMCs. Diminished calcification is observed in mice treated with AG1478 or ML290. The late stage treatments allow the assessment of potential reversibility of calcification associated with EGFR inhibition and RXFP1 agonism. Decreased mineral in the treated groups likely lead to a decrease in EV characteristics associated with calcification.

Example 6—EGFR Inhibition and RXFP1 Agonism Alter SMC Caveolae Trafficking to Prevent Calcifying EV Formation Interactions between these receptors and caveolin-1, changes in caveolin-1 phosphorylation and trafficking following EGFR inhibition and RXFP1 agonism, and subsequent altered properties of EVs due to targeting the receptors are studies to investigate the potential caveolae-dependent mechanisms by which EGFR inhibition and RXFP1 agonism prevent calcification.

Figure 13:
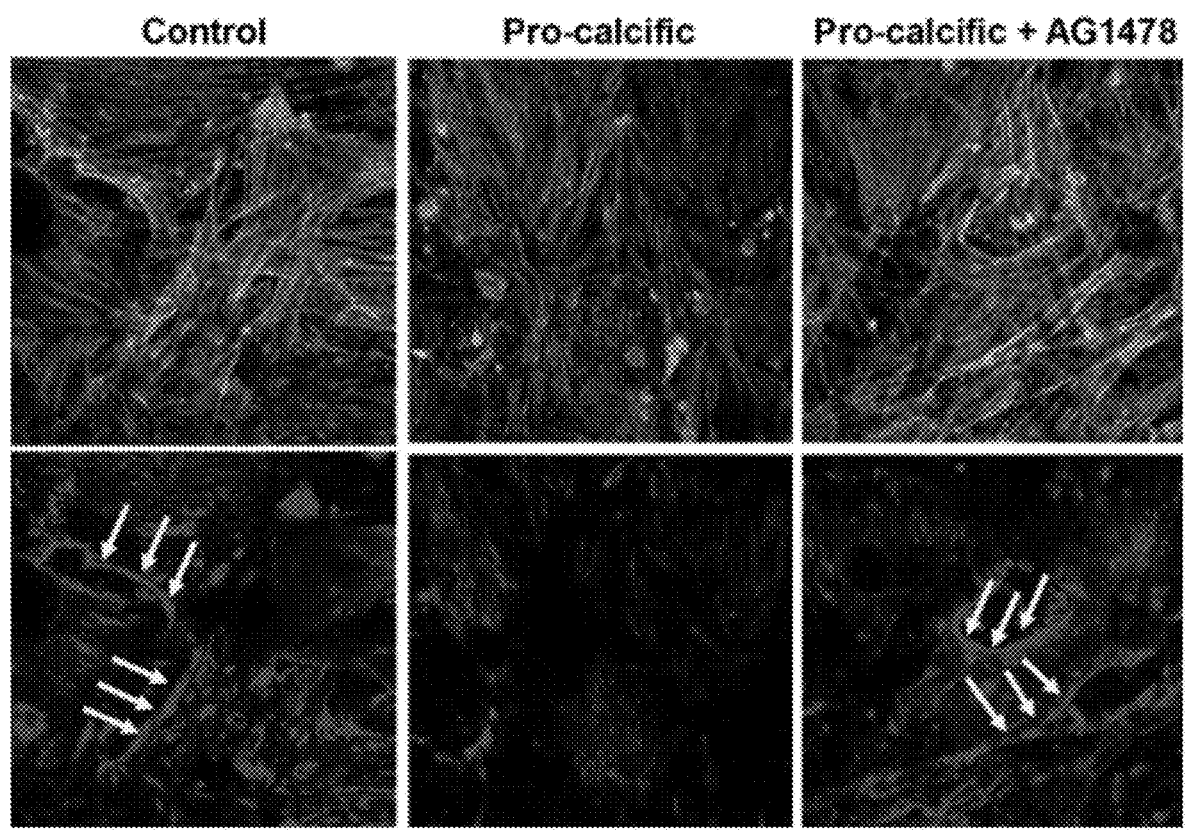
FIG. 13 shows that AG1478 preserves caveolin-1 (red) plasma membrane localization in pro-calcific conditions. Actin filaments are shown in green.

EGFR is a known caveolin-1 interactor with tyrosine kinase activity that can alter caveolin-1 intracellular translocation. Interactions between caveolin-1 and EGFR also suppress EGFR kinase activity. Thus, inhibition of EGFR kinase activity promotes stable interactions between EGFR and caveolin-1 at the plasma membrane, leading to reduced calcifying EV formation. The data show that EGFR tyrosine kinase inhibition with AG1478 decreases EV caveolin-1 without affecting intracellular caveolin-1 levels (FIG. 8). Immunofluorescence data show that this may be due to altered caveolin-1 trafficking (FIG. 13).

Figure 14:
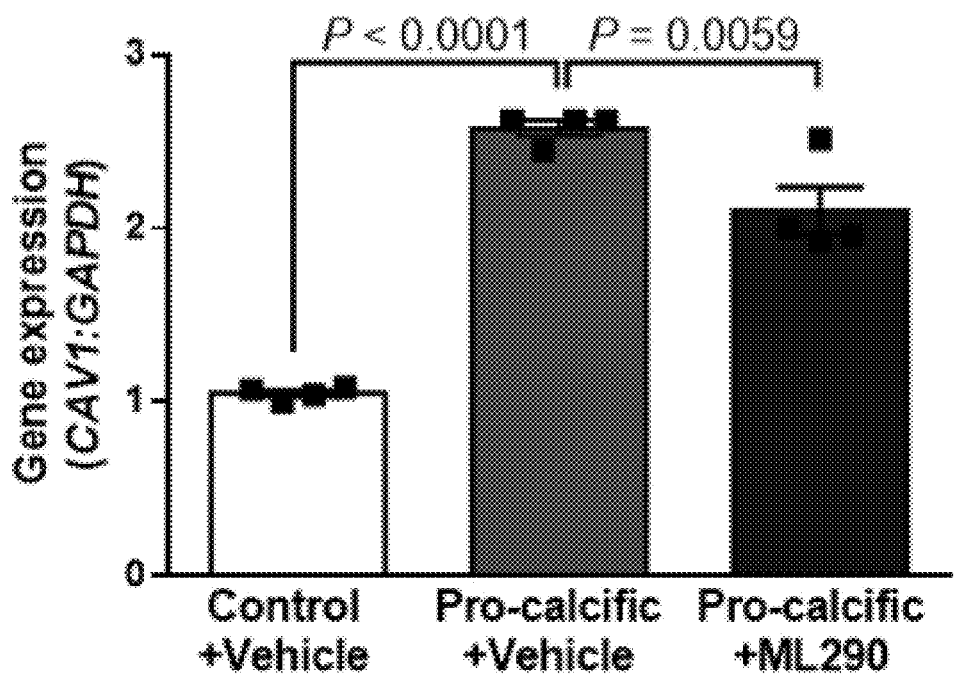
FIG. 14 show that ML290 reduces caveolin-1 expression in pro-calcific SMC culture.

A confocal optical section shows that caveolin-1 (red fluorescence) redistributed from the SMC periphery in control media to intracellular compartments in pro-calcific media. EGFR inhibition with 1 µM AG1478 maintained the peripheral localization of caveolin-1. The vasodilatory effects of RXFP1 agonism occurs through interactions within caveolae on endothelial cells. G-protein-coupled receptors (GPCRs), such as RXFP1, use caveolae scaffolding domains to regulate interactions with other proteins and activate downstream signaling. Treating SMCs with ML290 for 24 h decreases caveolin-1 gene expression in pro-calcific conditions (FIG. 14). RXFP1 agonism may stabilize existing caveolae, leading to the observed decreased caveolin-1 turnover. RXFP1 agonist-induced stabilization of caveolae may prevent the formation of calcifying EVs.

Mechanical stimulation induces caveolin-1 redistribution to EVs within 3 days (FIG. 3). Early osteogenic changes in SMCs are observed after 7 days in pro-calcific media culture, and the elaboration of calcifying EVs peaks after 14 days in this media. Thus, alterations in caveolae trafficking after 3, 7, and 14 days are assessed in the culture conditions: 1) static SMCs cultured in control media; 2) static SMCs cultured in pro-calcific media; 3) SMCs exposed to cyclic 10% mechanical strain in control media; and 4) SMCs exposed to cyclic 10% mechanical strain for pro-calcific media.

To test the effect of EFGR inhibition and RXFP1 agonism, 1 µM AG1478 or ML290 is used in these conditions. Changes in SMC phenotype are assayed in the culture conditions and in response to the small molecule treatments by measuring expression of osteogenic and SMC relevant genes at the time points considered. In vitro mineralization is assessed using alizarin red S staining, extraction, and colorimetric analyses after 21 days in culture.

To determine changes in caveolin-1 associated with the culture conditions and treatments, western blotting and immunofluorescence are used to assay caveolin-1 phosphorylation on tyrosine 14. This site is associated with changes in EGFR activity and caveolae internalization. Immunofluorescence is then used to assess the localization of caveolin-1 within the SMCs for the different culture conditions at these time points. Western blotting is used to quantify caveolin-1 in EVs relative to SMC lysates.

Because Golgi trafficking is required for TNAP activation in SMCs, CellLight Golgi transfection (Molecular Probes) is used to determine the potential intracellular target of the observed redistribution. Size and charge of EVs collected from these conditions at each time point are also assessed by nanopipette analyses, and mineralization potential is measured using the collagen hydrogel platform.

To assess physical interactions between the target receptors and caveolae that may affect trafficking and calcifying EV formation, caveolin-1 is immunoprecipitated from SMC lysates. Western blotting is performed for EGFR and RXFP1 for each of the treatment groups at each time point considered. For added rigor in the analyses, the receptors are immunoprecipitated and the presence of caveolin-1 is assessed. To ensure specificity of the immunoprecipitation, these analyses are performed following siRNA-mediated knockdown of caveolin-1. Finally, the caveolae-enriched membrane (using the density-based ultracentrifugation procedure outlined in Aim 1) is isolated to measure the caveolae localization of the receptors.

Formation of calcifying EVs requires cytoplasmic vesicles to traffic to the Golgi, assimilate active TNAP, and release from SMCs after trafficking back to the plasma membrane. The cytoplasmic vesicles originate from caveolae. EGFR inhibition and RXFP1 agonism with clinically relevant small molecules can arrest caveolae in the plasma membrane to prevent the initiating events that result in calcifying EV formation. Thus, increased receptor-caveolin-1 interactions and a decrease in calcifying EV release in SMCs treated with either AG1478 or ML290 can be observed.

Figure 15:
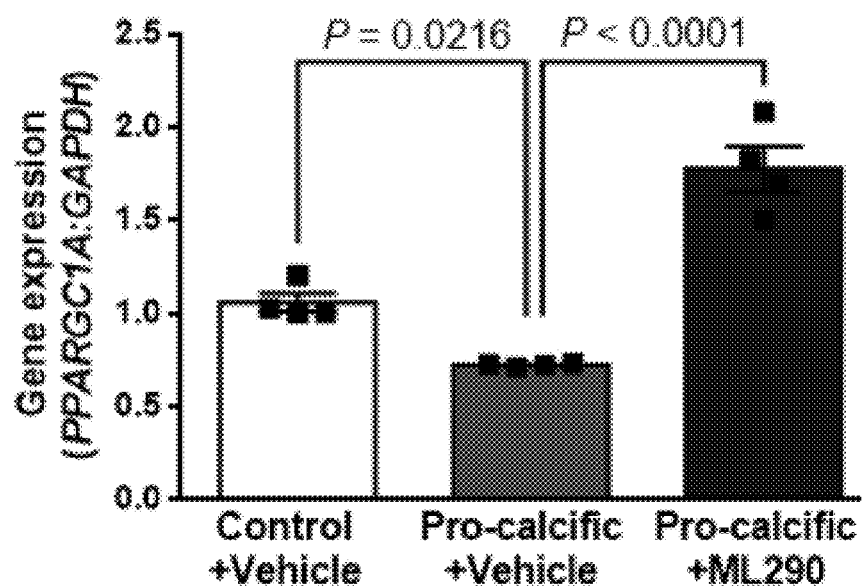
FIG. 15 shows that ML290 treatment increased expression of PPARGC1A in pro-calcific media.

The modulation of a different GPCR, the serotonin 2B receptor, alters intracellular trafficking to prevent calcification by aortic valve cells. Both 5-HT2B and RXFP1 can modulate vascular tone through interactions with nitric oxide synthase—a known caveolin-1 interactor. RXFP1 may, however, affect caveolin-1 protein stability directly. Peroxisome Proliferator-Activated Receptor γ (PPARγ) activation promotes lysosomal degradation of caveolin-1 in pulmonary artery SMCs. RXFP1 activity has been shown to activate PPARγ. The result shows that ML290 treatment increases PPARGC1A (a critical PPARγ activator) gene expression in SMCs cultured in pro-calcific media (FIG. 15). Therefore, thus result indicates the potential mechanism for the observed anti-calcific effects of ML290.

The subject invention yields pre-clinical data necessary to establish EGFR inhibition and/or RXFP1 agonism for treatment of CKD-associated medial calcification. Both targets have demonstrated clinical safety, and CKD patients represent an identifiable population in need of therapeutics for vascular calcification.

In summary, EGFR inhibition and RXFP1 agonism prevent SMC calcification in vitro. RXFP1 agonism also mitigates intimal atherosclerotic and medial CKD calcification in vivo. Both EGFR inhibition and RXFP1 agonism demonstrate clinical safety. Using two small molecules, an EGFR inhibitor and a novel RXFP1 agonist, the efficacy of targeting caveolae trafficking to treat SMC-driven medial calcification in the CKD mouse model are tested above. Mice are either treated at the onset of the high phosphate diet that induces vascular calcification or following two weeks of the diet. These studies allow the assessment of the potential of the treatments to reverse calcification once mineralization has already begun. Analyses of size, charge, and lipid properties of EVs isolated from the mice connect the in vivo modulation of EV formation to the caveolae-dependent mechanisms studied above.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

We claim:

1. A method for treating vascular calcification comprising administering, to a subject in need of such treatment, a pharmaceutical composition comprising an agonist targeting relaxin family peptide receptor 1 (RXFP1), the agonist being ML290.

2. The method of claim 1, the vascular calcification being cardiovascular calcification.

3. The method of claim 1, the vascular calcification being medial vascular calcification or intimal atherosclerotic calcification.

4. The method of claim 1, the pharmaceutical composition further comprising one or more agonists targeting RXFP1 selected from the group consisting of a relaxin peptide and a non-peptide small molecule RXFP1 agonist.

5. The method of claim 1, the subject being a human.

6. The method of claim 1, the subject having been diagnosed with chronic kidney disease (CKD), diabetes, hyperparathyroidism, hyperphosphatemia, a vitamin D disorder, a vitamin K disorder, osteoporosis, Kawasaki disease, arterial calcification due to deficiency of CD73 (ACDC), idiopathic basal ganglia calcification (IBGC), pseudoxanthoma elasticum (PXE), rheumatoid arthritis, Singleton-Merten syndrome, β-thalassemia, atherosclerosis, hyperlipidemia, hypertension, amputation, congenital bicuspid valve, and/or rheumatic heart disease.

7. The method of claim 1, the administration being local, oral, transdermal, or parenteral, administration.

8. The method of claim 1, the vascular calcification being aortic calcification.

9. The method of claim 1, further comprising 1) evaluating mineral formation by vascular smooth muscle cells, and/or 2) evaluating PPARGC1A and/or caveolin-1 gene expression in vascular smooth muscle cells.

10. A method for reducing mineral nucleation and deposition in a vascular wall, the method comprising administering, to a subject in need of such reduction, a pharmaceutical composition comprising an agonist targeting relaxin family peptide receptor 1 (RXFP1), the agonist being ML290.

11. The method of claim 10, the pharmaceutical composition further comprising one or more RXFP1 agonists selected from the group consisting of a relaxin peptide and a non-peptide small molecule RXFP1 agonist.

12. The method of claim 10, the subject being a human having been diagnosed with CKD or atherosclerosis.

13. The method of claim 10, the administration being local, oral, transdermal, or parenteral, administration.

14. The method of claim 10, the vascular wall being a cardiovascular wall.

15. The method of claim 10, the subject having been diagnosed with chronic kidney disease (CKD), diabetes, hyperparathyroidism, hyperphosphatemia, a vitamin D disorder, a vitamin K disorder, osteoporosis, Kawasaki disease, arterial calcification due to deficiency of CD73 (ACDC), idiopathic basal ganglia calcification (IBGC), pseudoxanthoma elasticum (PXE), rheumatoid arthritis, Singleton-Merten syndrome, β-thalassemia, atherosclerosis, hyperlipidemia, hypertension, amputation, congenital bicuspid valve, and/or rheumatic heart disease.

* * * * *